(12) United States Patent
Quake et al.

(10) Patent No.: US 9,487,802 B2
(45) Date of Patent: *Nov. 8, 2016

(54) COMPOSITIONS AND METHODS TO TREAT LATENT VIRAL INFECTIONS

(71) Applicant: THE BOARD OF TRUSTEES OF THE LELAND STANFORD JUNIOR UNIVERSITY, Palo Alto, CA (US)

(72) Inventors: Stephen R. Quake, Palo Alto, CA (US); Jianbin Wang, Palo Alto, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/790,748

(22) Filed: Jul. 2, 2015

(65) Prior Publication Data

US 2015/0376583 A1    Dec. 31, 2015

Related U.S. Application Data

(63) Continuation of application No. 14/725,888, filed on May 29, 2015.

(60) Provisional application No. 62/029,072, filed on Jul. 25, 2014, provisional application No. 62/005,395, filed on May 30, 2014.

(51) Int. Cl.
| | |
|---|---|
| *C12N 15/86* | (2006.01) |
| *C12N 9/16* | (2006.01) |
| *C12N 9/22* | (2006.01) |
| *A61K 38/00* | (2006.01) |
| *C12N 15/90* | (2006.01) |
| *C12N 15/113* | (2010.01) |

(52) U.S. Cl.
CPC .............. *C12N 15/907* (2013.01); *C12N 9/16* (2013.01); *C12N 9/22* (2013.01); *C12N 15/1133* (2013.01); *C12N 15/86* (2013.01); *A61K 38/00* (2013.01); *C12N 2310/10* (2013.01); *C12N 2330/51* (2013.01); *C12N 2810/60* (2013.01); *C12Y 301/00* (2013.01)

(58) Field of Classification Search
None
See application file for complete search history.

(56) References Cited

U.S. PATENT DOCUMENTS

| | | | |
|---|---|---|---|
| 4,897,355 A | 1/1990 | Eppstein et al. |
| 4,946,787 A | 8/1990 | Eppstein et al. |
| 5,049,386 A | 9/1991 | Eppstein et al. |
| 5,208,036 A | 5/1993 | Eppstein et al. |
| 5,356,802 A | 10/1994 | Chandrasegaran |
| 5,436,150 A | 7/1995 | Chandrasegaran |
| 5,466,468 A | 11/1995 | Schneider et al. |
| 5,487,994 A | 1/1996 | Chandrasegaran |
| 5,580,571 A | 12/1996 | Hostetler |
| 5,626,869 A | 5/1997 | Nyqvist et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,383,481 B1 | 5/2002 | Ikehara et al. |
| 6,410,248 B1 | 6/2002 | Greisman et al. |
| 6,453,242 B1 | 9/2002 | Eisenberg et al. |
| 6,534,261 B1 | 3/2003 | Cox, III et al. |
| 6,607,882 B1 | 8/2003 | Cox, III et al. |
| 6,890,554 B2 | 5/2005 | Jessee et al. |
| 7,166,298 B2 | 1/2007 | Jessee et al. |
| 8,697,359 B1 | 4/2014 | Zhang |
| 8,889,418 B2 | 11/2014 | Zhang et al. |
| 8,906,616 B2 | 12/2014 | Zhang et al. |
| 8,945,839 B2 | 2/2015 | Zhang |
| 8,993,233 B2 | 3/2015 | Zhang et al. |
| 2005/0064474 A1 | 3/2005 | Urnov et al. |
| 2006/0188987 A1 | 8/2006 | Guschin et al. |
| 2008/0131962 A1 | 6/2008 | Miller |
| 2009/0017543 A1 | 1/2009 | Wilkes et al. |
| 2010/0076057 A1 | 3/2010 | Sontheimer et al. |
| 2011/0023144 A1 | 1/2011 | Weinstein et al. |
| 2011/0177594 A1 | 7/2011 | Shushan et al. |
| 2012/0122213 A1 | 5/2012 | Lai et al. |
| 2013/0330778 A1 | 12/2013 | Zeiner et al. |
| 2014/0068797 A1 | 3/2014 | Doudna et al. |
| 2014/0186843 A1 | 7/2014 | Zhang et al. |
| 2014/0273037 A1 | 9/2014 | Wu |
| 2014/0273233 A1 | 9/2014 | Chen et al. |

(Continued)

FOREIGN PATENT DOCUMENTS

| | | |
|---|---|---|
| CN | 103911376 A | 7/2014 |
| WO | 91/16024 | 10/1991 |

(Continued)

OTHER PUBLICATIONS

Bloom et al. Inactivation of Hepatitis B Virus Replication in Cultured Cells and In Vivo with Engineered Transcription Activator-Like Effector Nucleases. Molecular Therapy vol. 21 No. 10, 1889-1897 Oct. 2013.*

Wikipedia. Transcription activator-like effector nuclease. https://en.wikipedia.org/wiki/Transcription_activator-like_effector_nuclease.*

Schiffer JT, Swan DA, Stone D, Jerome KR (2013) Predictors of Hepatitis B Cure Using Gene Therapy to Deliver DNA Cleavage Enzymes: A Mathematical Modeling Approach. PLoS Comput Biol 9(7): e1003131.*

(Continued)

*Primary Examiner* — Nick Zou
(74) *Attorney, Agent, or Firm* — Kilpatrick Townsend & Stockton LLP

(57) ABSTRACT

Viral infection is a persistent cause of human disease. Guided nuclease systems target the genomes of viral infections, rendering the viruses incapacitated.

20 Claims, 20 Drawing Sheets

(56) References Cited

U.S. PATENT DOCUMENTS

| | | |
|---|---|---|
| 2014/0295556 A1 | 10/2014 | Joung et al. |
| 2014/0315985 A1 | 10/2014 | May et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356958 A1 | 12/2014 | Mali et al. |
| 2014/0357523 A1 | 12/2014 | Zeiner et al. |
| 2015/0024500 A1 | 1/2015 | Yu et al. |
| 2015/0045546 A1 | 2/2015 | Siksnys et al. |
| 2015/0050699 A1 | 2/2015 | Siksnys et al. |
| 2015/0056705 A1 | 2/2015 | Conway et al. |
| 2015/0232881 A1 | 8/2015 | Glucksmann et al. |
| 2015/0232883 A1 | 8/2015 | Dahlman et al. |
| 2015/0353905 A1 | 12/2015 | Weiss et al. |
| 2015/0368670 A1 | 12/2015 | Quake et al. |
| 2016/0060655 A1 | 3/2016 | Quake et al. |

FOREIGN PATENT DOCUMENTS

| | | |
|---|---|---|
| WO | 91/17424 | 11/1991 |
| WO | 01/37868 A1 | 5/2001 |
| WO | 2005/028634 A2 | 3/2005 |
| WO | 2005/084190 A2 | 9/2005 |
| WO | 2007/071994 | 6/2007 |
| WO | 2007/097820 A2 | 8/2007 |
| WO | 2013/141680 | 9/2013 |
| WO | 2013/142578 | 9/2013 |
| WO | 2013/176772 | 11/2013 |
| WO | 2013/188037 | 12/2013 |
| WO | 2014/071235 | 5/2014 |
| WO | 2014/093479 | 6/2014 |
| WO | 2014/099744 | 6/2014 |
| WO | 2014/124226 | 8/2014 |
| WO | 2014/143381 | 9/2014 |
| WO | 2014/150624 | 9/2014 |
| WO | 2014/165349 | 10/2014 |
| WO | 2014/172470 | 10/2014 |
| WO | 2015/006290 | 1/2015 |
| WO | 2015/031775 | 3/2015 |
| WO | 2015/034872 | 3/2015 |
| WO | 2015/126927 A2 | 8/2015 |
| WO | 2015/153889 | 10/2015 |
| WO | 2015/184259 | 12/2015 |
| WO | 2015/184262 | 12/2015 |
| WO | 2015/184268 | 12/2015 |

OTHER PUBLICATIONS

Ebina et al. Harnessing the CRISPR/Cas9 system to disrupt latent HIV-1 provirus. Sci Rep. 2013;3:2510.*

Lee et al. Enhancing Transfection Efficiency Using Polyethylene Glycol Grafted Polyethylenimine and Fusogenic Peptide. Biotechnol. Bioprocess Eng. 2001, 6: 269-273.*

Bi et al. High-efficiency targeted editing of large viral genomes by RNAguided nucleases. PLoS Pathog, 2014, 10, e1004090.*

Green et al. Epstein-Barr virus infection and posttransplant lymphoproliferative disorder. Am J Transplant. Feb. 2013;13 Suppl 3:41-54.*

Bi, Yanwei et al., "High-Efficiency Targeted Editing of Large Viral Genomes by RNA-Guided Nucleases," PLOS Pathogens, vol. 10, No. 5, May 2014, p. e1004090.

Chen, Jieliang et al., "An Efficient Antiviral Strategy for Targeting Hepatitis B Vvirus Genome Using Transcription Activator-Like Effector Nucleases," Molecular Therapy, vol. 22, No. 2, Sep. 12, 2013, pp. 303-311.

Ebina, Hirotaka et al., "Harnessing the CRISPR/Cas9 system to disrupt latent HIV-1 provirus," Scientific Reports, vol. 3, Aug. 26, 2013, pp. 2510/1-2510/7.

Ran, F. Ann et al., "Double Nicking by RNA-guided CRISPR/Cas9 for Enhanced Genome Editing Specificity," Cell, vol. 154, No. 6, Sep. 12, 2013, pp. 1380-1389.

Belfort & Roberts, 1997, Homing endonucleases: keeping the house in order, Nucleic Acids Res 25(17):3379-3388.

Bernard, 2007, Gene expression of genital human papillomaviruses and considerations on potential antiviral approaches. Antivir.Ther. 7:219-237.

Bhaya et al., 2011, CRISPR-Cas systems in bacteria and archea: versitle small RNAs for adaptive defense and regulation, Annu Rev Genet 45:273-297.

Chang et al., 2013, Genome editing with RNA-guided Cas9 nuclease in zebrafish embryos, Cell Res 23:465-472.

Chen et al., 2013, Dynamic Imaging of Genomic Loci in Living Human Cells by an Optimized CRISPR/Cas System. Cell 155:1479-1491.

Cong et al., 2013, Multiplex Genome Engineering Using CRISPR/Cas Systems, Science 339:819-823.

Gilbert et al., 2013, CRISPR-mediated modular RNA-guided regulation of transcription in eukaryotes, Cell 154:442-451.

Glatzel et al., 2000, Adenoviral and adeno-associated viral transfer of genes to the peripheral nervous system PNAS 97(1):442-447.

Harrison et al., 2014, A CRISPR view of development, Genes and Development 28:1859-1872.

Horvath et al., 2010, CRISPR/Cas, the immune system of bacteria and archaea, Science 327:167-170.

Hoshino et al., 2008, The number of herpes simplex virus-infected neurons and the number of viral genome copies per neuron correlate with latent viral load in ganglia, Virology 372(1):56-63.

Hsu et al., 2014, Development and applications of CRISPR-Cas9 for genome engineering, Cell 157:1262.

Hsu, 2013, DNA targeting specificity of RNA-guided Cas9 nucleases, Nature Biotechnology 31(9):827-832.

Hu et al., 2014, RNA-directed gene editing specifically eradicates latent and prevents new HIV-1 infection, PNAS 111(31):11461-6.

Hwang et al., 2013, Efficient genome editing in zebrafish using a CRISPR-Cas system, Nat. Biotechnol 31:227-229.

Jinek et al., 2013, RNA-programmed genome editing in human cells, eLife 2:e00471.

Jinek, 2012, A programmable dual-RNA-guided DNA endonuclease in adaptive bacterial immunity, Science 337:816-821.

Joung & Sander, 2013, TALENs: a widely applicable technology for targeted genome editing, Nat Rev Mol Cell Bio 14:49-55.

Liu et al., 2004, CMV enhancer/human PDGF-beta promoter for neuron specific transgene expression, Gene Ther 11(1):52-60.

Mali et al, 2013, RNA-guided human genome engineering via Cas9, Science 339:823-826.

Mali et al., 2013, Cas9 as a versatile tool for engineering biology, Nat Meth 10(10):957.

Munger et al., 2004, Mechanisms of human papillomavirus-induced oncogenesis, J Virol 78(21):11451-11460.

Naito et al., 2014, CRISPRdirect: software for designing CRISPR/Cas guide RNA with reduced off-target sites, Bioinformatics.

Nishimasu et al., 2014, Crystal structure of Cas9 in complex with guide RNA and target DNA, Cell 156:935-949.

Qi et al., 2013, Repurposing CRISP as an RNA-guided platform for sequence-specific control of gene expression, Cell 152:1173-1183.

Qu et al., 2013, Zinc-finger-nucleases mediate specific and efficient excision of HIV-1 proviral DAN from infected and latently infected human T cells, Nucl Ac Res 41(16):7771-7782.

Ruf et al., 1999, Epstein-Barr Virus Regulates c-MYC, Apoptosis, and Tumorigenicity in Burkitt Lymphoma, Molecular and Cellular Biology 19:1651-1660.

Schiffer, 2012, Targeted DNA mutagenesis for the cure of chronic viral infections, J Virol 88(17):8920-8936.

Schwank et al., 2013, Functional repair of CFTR by CRISPR/Cas9 in intestinal stem cell organoids of cystic fibrosis patients, Cell Stem Cell 13(6):653-8.

Silva et al., 2011, Meganucleases and other tools for targeted genome engineering, Curr Gene Ther 11(1):11-27.

Sternberg et al., 2014, DNA interrogation by the CRISPR RNA-guided endonuclease Cas9, Nature 507(7490):62-67.

Terns et al., 2011, CRISPR-based adaptive immune systems, Curr Op Microb 14:321-327.

Wah, et al., 1998, Structure of FokI has implications for DNA cleavage, PNAS 95:10564-10569.

(56) References Cited

OTHER PUBLICATIONS

Wang & Quake, 2014, RNA-guided endonuclease provides a therapeutic strategy to cure latent herpesviridae infection, PNAS 111(36):13157-13162.

Wang et al., 2013, One-step generation of mice carrying mutations in multiple genes by CRISPR/Cas-mediated genome engineering, Cell 153:910-918.

Westergaard et al., 2001, Modulation of keratinocyte gene expression and differentiation by PPAR-selective ligands and tetradecyltheioacetic acid, J Invest Dermatol 116(5):702-12.

Wiedenheft et al., 2012, RNA-guided genetic silencing systems in bacteria and archaea, Nature 482:331-338.

Xiao et al., 2013, Chromosomal deletions and inversions mediated by TALENS and CRISPR/Cas in zebrafish, Nucl Acids Res 1-11.

Xue et al., 2014, Efficient gene knock-out and knock-in with transgenic Cas9 in *Drosophila*, G3 4:925-929.

Yang et al., 2013, One-step generation of mice carrying reporter and conditional alleles by CRISPR/Cas-mediated genome enginneering, Cell 154:1370-1379.

Zheng & Baker, 2006, Papillomavirus genome structure, expression, and post-transcriptional regulation, Front Biosci 11:2286-2302.

Hui, S. et al., "High-efficiency loading, transfection, and fusion of cells by electroporation in two-phase polymer systems," Biophysical Journal, 71:1123-30, 1996.

\* cited by examiner normalized abundance

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Synthetic sgEBV1 guide RNA targeting Sequence

<400> SEQUENCE: 1
gccctggacc aacccggccc          20

<210> SEQ ID NO 2
<211> LENGTH: 20
<212> TYPE: DNA
<213> ORGANISM: Artificial Sequence
<220> FEATURE:
<223> OTHER INFORMATION: Synthetic sgEBV2 guide RNA targeting Sequence

<400> SEQUENCE: 2
ggccgctgcc ccgctccggg          20

<210> SEQ ID NO 3
<211> LENGTH: 19
<212> TYPE: DNA
<213> ORGANISM: Artificial Sequence
<220> FEATURE:
<223> OTHER INFORMATION: Synthetic sgEBV3 guide RNA targeting Sequence

<400> SEQUENCE: 3
ggaagacaat gtgccgcca           19

<210> SEQ ID NO 4
<211> LENGTH: 20
<212> TYPE: DNA
<213> ORGANISM: Artificial Sequence
<220> FEATURE:
<223> OTHER INFORMATION: Synthetic sgEBV4 guide RNA targeting Sequence

<400> SEQUENCE: 4
tctggaccag aaggctccgg          20

<210> SEQ ID NO 5
<211> LENGTH: 20
<212> TYPE: DNA
<213> ORGANISM: Artificial Sequence
<220> FEATURE:
<223> OTHER INFORMATION: Synthetic sgEBV5 guide RNA targeting Sequence

<400> SEQUENCE: 5
gctgccgcgg agggtgatga          20

<210> SEQ ID NO 6
<211> LENGTH: 20
<212> TYPE: DNA
<213> ORGANISM: Artificial Sequence
<220> FEATURE:
<223> OTHER INFORMATION: Synthetic sgEBV6 guide RNA targeting Sequence

<400> SEQUENCE: 6
ggtggcccac cgggtccgct          20

<210> SEQ ID NO 7
<211> LENGTH: 20
<212> TYPE: DNA
<213> ORGANISM: Artificial Sequence

```
<220> FEATURE:
<223> OTHER INFORMATION: Synthetic sgEBV7 guide RNA targeting Sequence

<400> SEQUENCE: 7
gtcctcgagg gggccgtcgc                                                        20
```

COMPOSITIONS AND METHODS TO TREAT LATENT VIRAL INFECTIONS

CROSS-REFERENCE TO RELATED APPLICATION(S)

The present application is a continuation of U.S. patent application Ser. No. 14/725,888, filed May 29, 2015, which claims priority to, and the benefit of, both U.S. Provisional Patent Application Ser. No. 62/005,395, filed May 30, 2014, and U.S. Provisional Patent Application Ser. No. 62/029,072, filed Jul. 25, 2014, the contents of which are incorporated by reference.

REFERENCE TO A SEQUENCE LISTING

The Sequence Listing written in file SequenceListing_079455-000621US-0950003.txt, created on Sep. 17, 2015, 1,960 bytes, machine format IBM-PC, MS-Windows operating system, is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under contracts CA139490, CA151459, HL099995, and HL099999 awarded by the National Institutes of Health. The Government has certain rights in the invention.

FIELD OF THE INVENTION

The invention generally relates to compositions and methods for selectively treating viral infections using a guided nuclease system.

BACKGROUND

Viral infections are a significant medical problem. Various antiviral treatments are available but they generally are directed to interrupting the replicating cycle of the virus. Thus, a particularly difficult problem is latent viral infection, as there is no effective treatment to eradicate the virus from host cells. Since latent infection can evade immune surveillance and reactivate the lytic cycle at any time, there is a persistent risk throughout the life. The majority of antiviral drug development has been focused on protein targets and such approaches have not been successful in eradicating the virus.

One example of a latent viral infection that is a particular problem is the herpesviridae virus family. Herpes is one of the most widespread human pathogens, with more than 90% of adults having been infected with at least one of the eight subtypes of herpes viruse. Latent infection persists in most people; and about 16% of Americans between the ages of 14 and 49 are infected with genital herpes, making it one of the most common sexually transmitted diseases. Due to latency, there is no cure for genital herpes or for herpes simplex virus type 2 (HSV-2). Once infected, a host carries the herpes virus indefinitely, even when not expressing symptoms. Similarly, human papillomavirus, or HPV is a common virus in the human population, where more than 75% of women and men will have this type of infection at one point in their life. High-risk oncogenic HPV types are able to integrate into the DNA of the cell that can result in cancer, specifically cervical cancer. Similar to the herpesviridae virus family, HPV may remain latent.

The Epstein-Barr virus (EBV), also called human herpesvirus 4 (HHV-4) is another common virus in humans. Epstein-Barr is known as the cause of infectious mononucleosis (glandular fever), and is also associated with particular forms of cancer, such as Hodgkin's lymphoma, Burkitt's lymphoma, nasopharyngeal carcinoma, and conditions associated with human immunodeficiency virus (HIV) such as hairy leukoplakia and central nervous system lymphomas. There is evidence that infection with the virus is associated with a higher risk of certain autoimmune diseases, especially dermatomyositis, systemic lupus erythematosus, rheumatoid arthritis, Sjögren's syndrome, and multiple sclerosis. During latency, the EBV genome circularizes and resides in the cell nucleus as episomes. To date, however, no EBV vaccine or treatment exists.

Viruses, such as the herpesviridae virus family, including EBV, and HPV have the ability to lie dormant within a cell indefinitely and not be fully eradicated even after treatment. The result is that the virus can reactivate and begin producing large amounts of viral progeny without the host being infected by any new outside virus. In the latent state, the viral genome persists within the host cells as episomes; stabilized and floating in the cytoplasm or nucleus. For these latent viruses, it has not been possible to find therapeutic approaches which completely eradicate such infections.

SUMMARY

The invention provides methods for selectively treating viral infections using a guided nuclease system. Methods of the invention may be used to remove viral or other foreign genetic material from a host organism, without interfering the integrity of the host's genetic material. A nuclease may be used to target viral nucleic acid, thereby interfering with viral replication or transcription or even excising the viral genetic material from the host genome. The nuclease may be specifically targeted to remove only the viral nucleic acid without acting on host material either when the viral nucleic acid exists as a particle within the cell or when it is integrated into the host genome. Targeting the viral nucleic acid can be done using a sequence-specific moiety such as a guide RNA that targets viral genomic material for destruction by the nuclease and does not target the host cell genome. In some embodiments, a CRISPR/Cas9 nuclease and guide RNA (gRNA) that together target and selectively edit or destroy viral genomic material is used. The CRISPR (clustered regularly interspaced short palindromic repeats) is a naturally-occurring element of the bacterial immune system that protects bacteria from phage infection. The guide RNA localizes the CRISPR/Cas9 complex to a viral target sequence. Binding of the complex localizes the Cas9 endonuclease to the viral genomic target sequence causing breaks in the viral genome. Other nuclease systems can be used including, for example, zinc finger nucleases, transcription activator-like effector nucleases (TALENs), meganucleases, or any other system that can be used to degrade or interfere with viral nucleic acid without interfering with the regular function of the host's genetic material.

In certain aspects, the invention provides a method for treating a viral infection. The method includes introducing into a cell a nuclease and a sequence-specific targeting moiety. The nuclease is targeted to viral nucleic acid by means of the sequence-specific targeting moiety and the nuclease cleaves the viral nucleic acid without interfering with a host genome. The nuclease may be, for example, a zinc-finger nuclease, a transcription activator-like effector nuclease, and a meganuclease. In a preferred embodiment, the nuclease is a Cas9 endonuclease and the sequence-specific targeting moiety comprises a guide RNA. The cleaving step can make one or more single or double stranded breaks in the viral nucleic acid. The method may further include inserting a polynucleotide or re-joining the cleaved ends with a piece of the viral nucleic acid removed. The host may be a living subject such as a human patient and the steps may be performed in vivo.

The method may be used to target viral nucleic acid in any form or at any stage in the viral life cycle. For example, the method may be used to digest viral RNA or DNA. The targeted viral nucleic acid may be present in the host cell as independent particles. In a preferred embodiment, the viral infection is latent and the viral nucleic acid is integrated into the host genome. Any suitable viral nucleic acid may be targeted for cleavage and digestion. In certain embodiments, the targeted virus includes one or more of herpes simplex virus (HSV)-1, HSV-2, varicella zoster virus (VZV), cytomegalovirus (CMV), human herpesvirus (HHV)-6, HHV-7, Kaposi's sarcoma-associated herpesvirus (KSHV), JC virus, BK virus, parvovirus b19, adeno-associated virus (AAV), and adenovirus. In some embodiments, the targeted virus or viruses include one or more of Adenovirus, Herpes simplex, type 1, Herpes simplex, type 2, Varicella-zoster virus, Epstein-barr virus, Human cytomegalovirus, Human herpesvirus, type 8, Human papillomavirus, BK virus, JC virus, Smallpox, Hepatitis B virus, Human bocavirus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, Human immunodeficiency virus (HIV), Influenza virus, Guanarito virus, Junin virus, Lassa virus, Machupo virus, Sabiá virus, Crimean-Congo hemorrhagic fever virus, Ebola virus, Marburg virus, Measles virus, Mumps virus, Parainfluenza virus, Respiratory syncytial virus, Human metapneumovirus, Hendra virus, Nipah virus, Rabies virus, Hepatitis D, Rotavirus, Orbivirus, Coltivirus, and Banna virus.

The nuclease and sequence-specific targeting moiety may be introduced into the cell using a vector. For example, a viral vector that encodes the nuclease and sequence-specific targeting moiety may be used. The viral vector may be retrovirus, lentivirus, adenovirus, herpesvirus, poxvirus, alphavirus, vaccinia virus or adeno-associated viruses. In some embodiments, a non-viral vector is used. A suitable non-viral vector may include, for example, a nanoparticle, a cationic lipid, a cationic polymer, metallic nanoparticle, a nanorod, a liposome, microbubbles, a cell-penetrating peptide, a liposphere, polyethyleneglycol (PEG). The cell may be prompted to take up the vector by, e.g., ultrasound or electroporation.

Aspects of the invention provide a composition for treatment of a viral infection. The composition includes a nuclease and a sequence-specific targeting moiety that targets the nuclease to viral nucleic acid in vivo within a host cell thereby causing the nuclease to cleave the viral nucleic acid without interfering with host nucleic acid. In certain embodiments, the nuclease is a Cas9 endonuclease and the sequence-specific binding module comprises a guide RNA that specifically targets a portion of a viral genome. The Cas9 endonuclease and the guide RNA may be co-expressed in a host cell infected by a virus. In some embodiments, the nuclease is one selected from the list consisting of a zinc-finger nuclease, a transcription activator-like effector nuclease, and a meganuclease.

The viral nucleic acid to be cleaved may include one or more of, e.g., herpes simplex virus (HSV)-1, HSV-2, varicella zoster virus (VZV), cytomegalovirus (CMV), human herpesvirus (HHV)-6, HHV-7, Kaposi's sarcoma-associated herpesvirus (KSHV), JC virus, BK virus, parvovirus b19, adeno-associated virus (AAV), and adenovirus, or others.

In some aspects, the invention provides a composition for treatment of a viral infection. The composition includes nucleic acid that encodes a nuclease and a sequence-specific targeting moiety that targets the nuclease to viral nucleic acid thereby causing the nuclease to cleave the viral nucleic acid without interfering with host nucleic acid. In some embodiments, the sequence-specific targeting moiety uses a guide RNA, which may be complementary to a portion of a viral genome. The guide RNA may be designed to cause the nuclease to cleave the viral genome within a feature that is necessary for viral function. The feature may be, for example, a viral replication origin, a terminal repeat, a replication factor binding site, a promoter, a coding sequence, or a repetitive region. The nucleic acid is provided within a delivery vector which may be a viral vector such as an adeno-associated virus. The vector could include any of retrovirus, lentivirus, adenovirus, herpesvirus, poxvirus, alphavirus, vaccinia virus, a nanoparticle, a cationic lipid, a cationic polymer, a metallic nanoparticle, a nanorod, a liposome, microbubbles, cell-penetrating peptide, a liposphere, or polyethyleneglycol (PEG).

Methods and compositions of the invention may be used to deliver a CRISPR/gRNA/Cas9 complex to a cell (including entire tissues) that is infected by a virus. a guide RNA may be designed to target multiple sites on the viral genome in order to disrupt viral nucleic acid and reduce the chance that it will functionally recombine. The CRISPR/gRNA/Cas9 complexes of the invention can be delivered by viral, non-viral or other methods to effectuate transfection. CRISPR/gRNA/Cas9 complexes are preferably designed to target viral genomic material and not genomic material of the host. In some embodiments, the targeted viral nucleic acid is associated with a virus that causes latent infection. Latent viruses may be, for example, human immunodeficiency virus, human T-cell leukemia virus, Epstein-Barr virus, human cytomegalovirus, human herpesviruses 6 and 7, herpes simplex virus types 1 and 2, varicella-zoster virus, measles virus, or human papovaviruses. Aspects of the invention allow for CRISPR/gRNA/Cas9 complexes to be designed to target any virus, latent or active.

The presented methods allow for viral genome editing or destruction, which results in the inability of the virus to proliferate and/or induces apoptosis in infected cells, with no observed cytotoxicity to non-infected cells. A CRISPR/gRNA/Cas9 complex is designed to selectively target viral genomic material (DNA or RNA), delivering the CRISPR/gRNA/Cas9 complex to a cell containing the viral genome, and cutting the viral genome in order to incapacitate the virus. A viral infection can thus be treated by targeted disruption of viral genomic function or by digestion of viral nucleic acid via one or multiple breaks caused by targeting sites for endonuclease action in the viral genome. In some embodiments, methods of the invention may be used for transfection of a host cell with CRISPR/gRNA/Cas9 to completely suppressed cell proliferation and/or induce apoptosis in infected cells.

BRIEF DESCRIPTION OF THE DRAWINGS

(FIG. 1A) Scheme of CRISPR/Cas plasmids, adapted from Cong L et al. (2013) Multiplex Genome Engineering Using CRISPR/Cas Systems. Science 339:819-823. (FIG. 1B) Effect of oriP on transfection efficiency in Raji cells. Both Cas9 and Cas9-oriP plasmids have a scrambled guide RNA. (FIG. 1C) CRISPR guide RNA targets along the EBV reference genome. Green, red and blue represent three different target sequence categories.

(FIG. 2A) Genome context around guide RNA sgEBV2 and PCR primer locations. (FIG. 2B) Large deletion induced by sgEBV2. Lane 1-3 are before, 5 days after, and 7 days after sgEBV2 treatment, respectively. (FIG. 2C) Genome context around guide RNA sgEBV3/4/5 and PCR primer locations. (FIG. 2D) Large deletions induced by sgEBV3/5 and sgEBV4/5. Lane 1 and 2 are 3F/5R PCR amplicons before and 8 days after sgEBV3/5 treatment. Lane 3 and 4 are 4F/5R PCR amplicons before and 8 days after sgEBV4/5 treatment. (FIGS. 2E and F) Sanger sequencing confirmed genome cleavage and repair ligation 8 days after sgEBV3/5 (FIG. 2E) and sgEBV4/5 (FIG. 2F) treatment. Blue and white background highlights the two ends before repair ligation.

(FIG. 3A) Cell proliferation curves after different CRISPR treatments. Five independent sgEBV1-7 treatments are shown here. (FIGS. 3B-D) Flow cytometry scattering signals before (FIG. 3B), 5 days after (FIG. 3C) and 8 days after (FIG. 3D) sgEBV1-7 treatments. (FIG. 3E-G) Annexin V Alexa647 and DAPI staining results before (FIG. 3E), 5 days after (FIG. 3F) and 8 days after (FIG. 3G) sgEBV1-7 treatments. Blue and red correspond to subpopulation P3 and P4 in (FIGS. 3B-D). (FIGS. 3H and I) Microscopy revealed apoptotic cell morphology after sgEBV1-7 treatment. (FIGS. 3J-M) Nuclear morphology before (FIG. 3J) and after (FIGS. 3K-M) sgEBV1-7 treatment.

(FIG. 4A) EBV load after different CRISPR treatments by digital PCR. Cas9 and Cas9-oriP had two replicates, and sgEBV1-7 had 5 replicates. (FIGS. 4B and C) Microscopy of captured single cells for whole-genome amplification. (FIG. 4D) Histogram of EBV quantitative PCR Ct values from single cells before treatment. (FIG. 4E) Histogram of EBV quantitative PCR Ct values from single live cells 7 days after sgEBV1-7 treatment. Red dash lines in (FIG. 4D) and (FIG. 4E) represent Ct values of one EBV genome per cell.

DETAILED DESCRIPTION

The invention generally relates to compositions and methods for selectively treating viral infections using a guided nuclease system. Methods of the invention are used to incapacitate or disrupt viral nucleic acid within a cell through nuclease activity such as single- or double-stranded breaks, cleavage, digestion, or editing. Methods of the invention may be used for systematically causing large or repeated deletions in the genome, reducing the probability of reconstructing the full genome.

i. Treating Infected Cell

Figure 9:
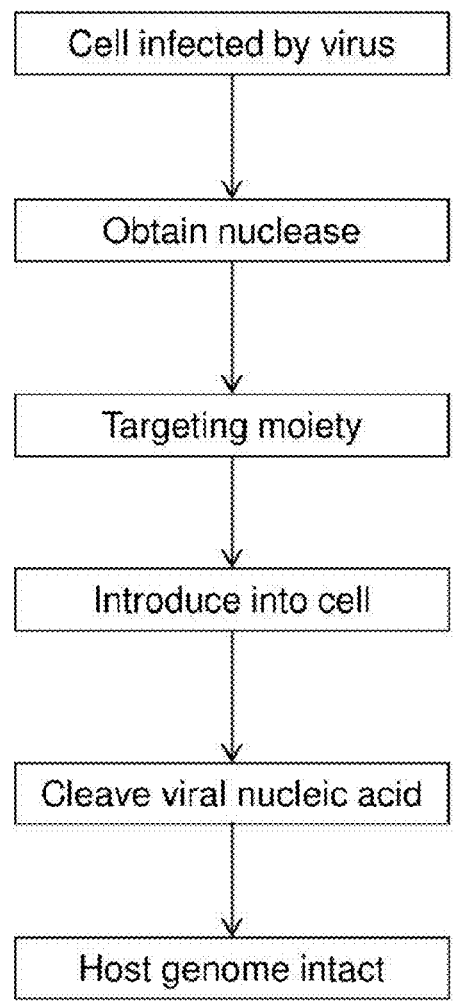
FIG. 9 diagrams a method of the invention.

FIG. 9 diagrams a method of treating a cell infected with a virus. Methods of the invention are applicable to in vivo treatment of patients and may be used to remove any viral genetic material such as genes of virus associated with a latent viral infection. Methods may be used in vitro, e.g., to prepare or treat a cell culture or cell sample. When used in vivo, the cell may be any suitable germ line or somatic cell and compositions of the invention may be delivered to specific parts of a patient's body or be delivered systemically. If delivered systemically, it may be preferable to include within compositions of the invention tissue-specific promoters. For example, if a patient has a latent viral infection that is localized to the liver, hepatic tissue-specific promotors may be included in a plasmid or viral vector that codes for a targeted nuclease.

Figure 12:
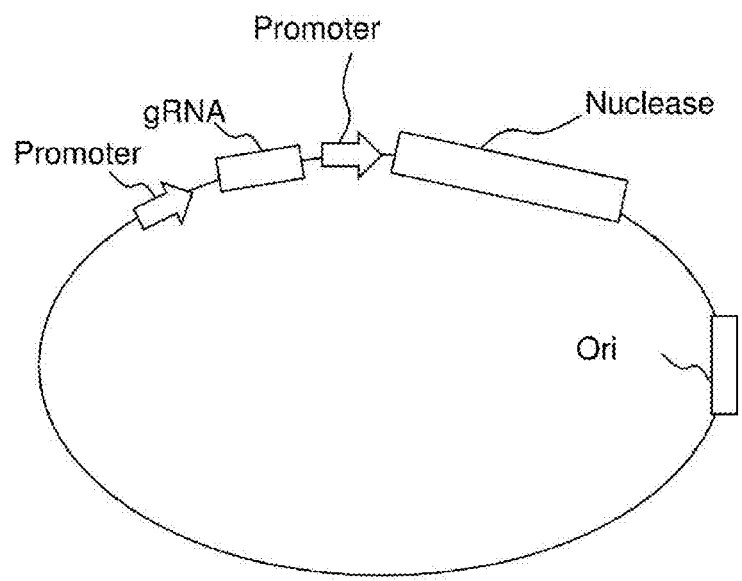
FIG. 12 shows a composition for treating a viral infection.

FIG. 12 shows a composition for treating a viral infection according to certain embodiments. The composition preferably includes a vector (which may be a plasmid, linear DNA, or a viral vector) that codes for a nuclease and a targeting moiety (e.g., a gRNA) that targets the nuclease to viral nucleic acid. The composition may optionally include one or more of a promoter, replication origin, other elements, or combinations thereof as described further herein.

ii. Nuclease

Methods of the invention include using a programmable or targetable nuclease to specifically target viral nucleic acid for destruction. Any suitable targeting nuclease can be used including, for example, zinc-finger nucleases (ZFNs), transcription activator-like effector nucleases (TALENs), clustered regularly interspaced short palindromic repeat (CRISPR) nucleases, meganucleases, other endo- or exo-nucleases, or combinations thereof. See Schiffer, 2012, Targeted DNA mutagenesis for the cure of chronic viral infections, J Virol 88(17):8920-8936, incorporated by reference.

CRISPR methodologies employ a nuclease, CRISPR-associated (Cas9), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas9 and guide RNA (gRNA) may be synthesized by known methods. Cas9/guide-RNA (gRNA) uses a non-specific DNA cleavage protein Cas9, and an RNA oligo to hybridize to target and recruit the Cas9/gRNA complex. See Chang et al., 2013, Genome editing with RNA-guided Cas9 nuclease in zebrafish embryos, Cell Res 23:465-472; Hwang et al., 2013, Efficient genome editing in zebrafish using a CRISPR-Cas system, Nat. Biotechnol 31:227-229; Xiao et al., 2013, Chromosomal deletions and inversions mediated by TALENS and CRISPR/Cas in zebrafish, Nucl Acids Res 1-11.

CRISPR(Clustered Regularly Interspaced Short Palindromic Repeats) is found in bacteria and is believed to protect the bacteria from phage infection. It has recently been used as a means to alter gene expression in eukaryotic DNA, but has not been proposed as an anti-viral therapy or more broadly as a way to disrupt genomic material. Rather, it has been used to introduce insertions or deletions as a way of increasing or decreasing transcription in the DNA of a targeted cell or population of cells. See for example, Horvath et al., Science (2010) 327:167-170; Terns et al., Current Opinion in Microbiology (2011) 14:321-327; Bhaya et al Annu Rev Genet (2011) 45:273-297; Wiedenheft et al. Nature (2012) 482:331-338); Jinek M et al. Science (2012) 337:816-821; Cong L et al. Science (2013) 339:819-823; Jinek M et al. (2013) eLife 2:e00471; Mali P et al. (2013) Science 339:823-826; Qi L S et al. (2013) Cell 152:1173-1183; Gilbert L A et al. (2013) Cell 154:442-451; Yang H et al. (2013) Cell 154:1370-1379; and Wang H et al. (2013) Cell 153:910-918).

In an aspect of the invention, the Cas9 endonuclease causes a double strand break in at least two locations in the genome. These two double strand breaks cause a fragment of the genome to be deleted. Even if viral repair pathways anneal the two ends, there will still be a deletion in the genome. One or more deletions using the mechanism will incapacitate the viral genome. The result is that the host cell will be free of viral infection.

In embodiments of the invention, nucleases cleave the genome of the target virus. A nuclease is an enzyme capable of cleaving the phosphodiester bonds between the nucleotide subunits of nucleic acids. Endonucleases are enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, cleave only at very specific nucleotide sequences. In a preferred embodiment of the invention, the Cas9 nuclease is incorporated into the compositions and methods of the invention, however, it should be appreciated that any nuclease may be utilized.

In preferred embodiments of the invention, the Cas9 nuclease is used to cleave the genome. The Cas9 nuclease is capable of creating a double strand break in the genome. The Cas9 nuclease has two functional domains: RuvC and HNH, each cutting a different strand. When both of these domains are active, the Cas9 causes double strand breaks in the genome.

In some embodiments of the invention, insertions into the genome can be designed to cause incapacitation, or altered genomic expression. Additionally, insertions/deletions are also used to introduce a premature stop codon either by creating one at the double strand break or by shifting the reading frame to create one downstream of the double strand break. Any of these outcomes of the NHEJ repair pathway can be leveraged to disrupt the target gene. The changes introduced by the use of the CRISPR/gRNA/Cas9 system are permanent to the genome.

In some embodiments of the invention, at least one insertion is caused by the CRISPR/gRNA/Cas9 complex. In a preferred embodiment, numerous insertions are caused in the genome, thereby incapacitating the virus. In an aspect of the invention, the number of insertions lowers the probability that the genome may be repaired.

In some embodiments of the invention, at least one deletion is caused by the CRISPR/gRNA/Cas9 complex. In a preferred embodiment, numerous deletions are caused in the genome, thereby incapacitating the virus. In an aspect of the invention, the number of deletions lowers the probability that the genome may be repaired. In a highly-preferred embodiment, the CRISPR/Cas9/gRNA system of the invention causes significant genomic disruption, resulting in effective destruction of the viral genome, while leaving the host genome intact.

TALENs uses a nonspecific DNA-cleaving nuclease fused to a DNA-binding domain that can be to target essentially any sequence. For TALEN technology, target sites are identified and expression vectors are made. Linearized expression vectors (e.g., by NotI) may be used as template for mRNA synthesis. A commercially available kit may be use such as the mMESSAGE mMACHINE SP6 transcription kit from Life Technologies (Carlsbad, Calif.). See Joung & Sander, 2013, TALENs: a widely applicable technology for targeted genome editing, Nat Rev Mol Cell Bio 14:49-55.

TALENs and CRISPR methods provide one-to-one relationship to the target sites, i.e. one unit of the tandem repeat in the TALE domain recognizes one nucleotide in the target site, and the crRNA, gRNA, or sgRNA of CRISPR/Cas system hybridizes to the complementary sequence in the DNA target. Methods can include using a pair of TALENs or a Cas9 protein with one gRNA to generate double-strand breaks in the target. The breaks are then repaired via non-homologous end joining or homologous recombination (HR).

Figure 8:
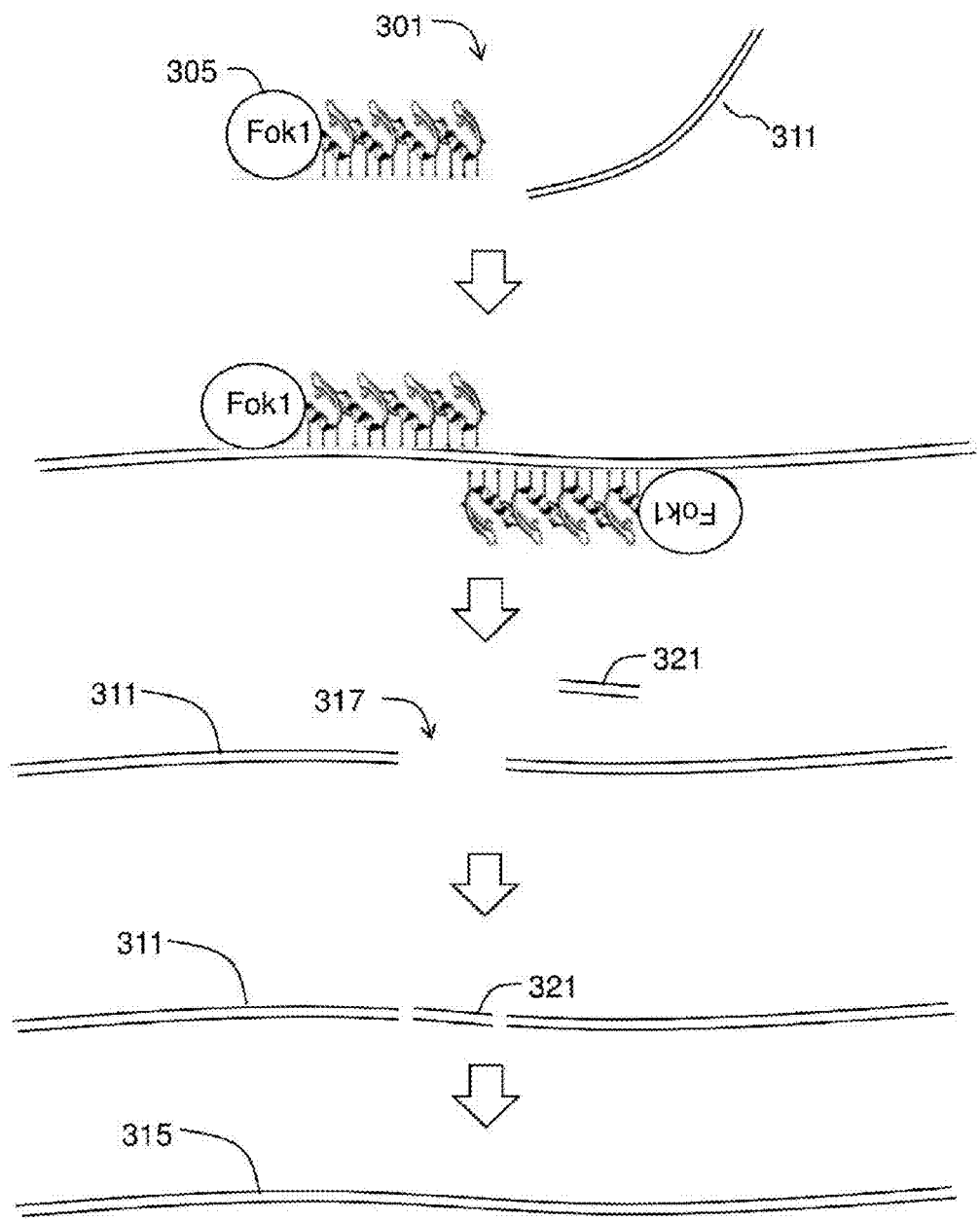
FIG. 8 shows the use of ZFNs.

FIG. 8 shows ZFN being used to cut viral nucleic acid. Briefly, the ZFN method includes introducing into the infected host cell at least one vector (e.g., RNA molecule) encoding a targeted ZFN 305 and, optionally, at least one accessory polynucleotide. See, e.g., U.S. Pub. 2011/0023144 to Weinstein, incorporated by reference The cell includes target sequence 311. The cell is incubated to allow expression of the ZFN 305, wherein a double-stranded break 317 is introduced into the targeted chromosomal sequence 311 by the ZFN 305. In some embodiments, a donor polynucleotide or exchange polynucleotide 321 is introduced. Swapping a portion of the viral nucleic acid with irrelevant sequence can fully interfere transcription or replication of the viral nucleic acid. Target DNA 311 along with exchange polynucleotide 321 may be repaired by an error-prone non-homologous end joining DNA repair process or a homology-directed DNA repair process.

Typically, a ZFN comprises a DNA binding domain (i.e., zinc finger) and a cleavage domain (i.e., nuclease) and this gene may be introduced as mRNA (e.g., 5' capped, polyadenylated, or both). Zinc finger binding domains may be engineered to recognize and bind to any nucleic acid sequence of choice. See, e.g., Qu et al., 2013, Zinc-finger-nucleases mediate specific and efficient excision of HIV-1 proviral DAN from infected and latently infected human T cells, Nucl Ac Res 41(16):7771-7782, incorporated by reference. An engineered zinc finger binding domain may have a novel binding specificity compared to a naturally-occurring zinc finger protein. Engineering methods include, but are not limited to, rational design and various types of selection. A zinc finger binding domain may be designed to recognize a target DNA sequence via zinc finger recognition regions (i.e., zinc fingers). See, for example, U.S. Pat. Nos. 6,607,882; 6,534,261 and 6,453,242, incorporated by reference. Exemplary methods of selecting a zinc finger recognition region may include phage display and two-hybrid systems, and are disclosed in U.S. Pat. No. 5,789,538; U.S. Pat. No. 5,925,523; U.S. Pat. No. 6,007,988; U.S. Pat. No. 6,013,453; U.S. Pat. No. 6,410,248; U.S. Pat. No. 6,140,466; U.S. Pat. No. 6,200,759; and U.S. Pat. No. 6,242,568, each of which is incorporated by reference.

A ZFN also includes a cleavage domain. The cleavage domain portion of the ZFNs may be obtained from any suitable endonuclease or exonuclease such as restriction endonucleases and homing endonucleases. See, for example, Belfort & Roberts, 1997, Homing endonucleases: keeping the house in order, Nucleic Acids Res 25(17):3379-3388. A cleavage domain may be derived from an enzyme that requires dimerization for cleavage activity. Two ZFNs may be required for cleavage, as each nuclease comprises a monomer of the active enzyme dimer. Alternatively, a single ZFN may comprise both monomers to create an active enzyme dimer. Restriction endonucleases present may be capable of sequence-specific binding and cleavage of DNA at or near the site of binding. Certain restriction enzymes (e.g., Type IIS) cleave DNA at sites removed from the recognition site and have separable binding and cleavage domains. For example, the Type IIS enzyme FokI, active as a dimer, catalyzes double-stranded cleavage of DNA, at 9 nucleotides from its recognition site on one strand and 13 nucleotides from its recognition site on the other. The FokI enzyme used in a ZFN may be considered a cleavage monomer. Thus, for targeted double-stranded cleavage using a FokI cleavage domain, two ZFNs, each comprising a FokI cleavage monomer, may be used to reconstitute an active enzyme dimer. See Wah, et al., 1998, Structure of FokI has implications for DNA cleavage, PNAS 95:10564-10569; U.S. Pat. No. 5,356,802; U.S. Pat. No. 5,436,150; U.S. Pat. No. 5,487,994; U.S. Pub. 2005/0064474; U.S. Pub. 2006/0188987; and U.S. Pub. 2008/0131962, each incorporated by reference.

Virus targeting using ZFN may include introducing at least one donor polynucleotide comprising a sequence into the cell. A donor polynucleotide preferably includes the sequence to be introduced flanked by an upstream and downstream sequence that share sequence similarity with either side of the site of integration in the chromosome. The upstream and downstream sequences in the donor polynucleotide are selected to promote recombination between the chromosomal sequence of interest and the donor polynucleotide. Typically, the donor polynucleotide will be DNA. The donor polynucleotide may be a DNA plasmid, a bacterial artificial chromosome (BAC), a yeast artificial chromosome (YAC), a viral vector, a linear piece of DNA, a PCR fragment, a naked nucleic acid, and may employ a delivery vehicle such as a liposome. The sequence of the donor polynucleotide may include exons, introns, regulatory sequences, or combinations thereof. The double stranded break is repaired via homologous recombination with the donor polynucleotide such that the desired sequence is integrated into the chromosome. In the ZFN-mediated process, a double stranded break introduced into the target sequence by the ZFN is repaired, via homologous recombination with the exchange polynucleotide, such that the sequence in the exchange polynucleotide may be exchanged with a portion of the target sequence. The presence of the double stranded break facilitates homologous recombination and repair of the break. The exchange polynucleotide may be physically integrated or, alternatively, the exchange polynucleotide may be used as a template for repair of the break, resulting in the exchange of the sequence information in the exchange polynucleotide with the sequence information in that portion of the target sequence. Thus, a portion of the viral nucleic acid may be converted to the sequence of the exchange polynucleotide. ZFN methods can include using a vector to deliver a nucleic acid molecule encoding a ZFN and, optionally, at least one exchange polynucleotide or at least one donor polynucleotide to the infected cell.

Meganucleases are endodeoxyribonucleases characterized by a large recognition site (double-stranded DNA sequences of 12 to 40 base pairs); as a result this site generally occurs only once in any given genome. For example, the 18-base pair sequence recognized by the I-SceI meganuclease would on average require a genome twenty times the size of the human genome to be found once by chance (although sequences with a single mismatch occur about three times per human-sized genome). Meganucleases are therefore considered to be the most specific naturally occurring restriction enzymes. Meganucleases can be divided into five families based on sequence and structure motifs: LAGLIDADG, GIY-YIG, HNH, His-Cys box and PD-(D/E)XK. The most well studied family is that of the LAGLIDADG proteins, which have been found in all kingdoms of life, generally encoded within introns or inteins although freestanding members also exist. The sequence motif, LAGLIDADG, represents an essential element for enzymatic activity. Some proteins contained only one such motif, while others contained two; in both cases the motifs were followed by ~75-200 amino acid residues having little to no sequence similarity with other family members. Crystal structures illustrates mode of sequence specificity and cleavage mechanism for the LAGLIDADG family: (i) specificity contacts arise from the burial of extended β-strands into the major groove of the DNA, with the DNA binding saddle having a pitch and contour mimicking the helical twist of the DNA; (ii) full hydrogen bonding potential between the protein and DNA is never fully realized; (iii) cleavage to generate the characteristic 4-nt 3'-OH overhangs occurs across the minor groove, wherein the scissile phosphate bonds are brought closer to the protein catalytic core by a distortion of the DNA in the central "4-base" region; (iv) cleavage occurs via a proposed two-metal mechanism, sometimes involving a unique "metal sharing" paradigm; (v) and finally, additional affinity and/or specificity contacts can arise from "adapted" scaffolds, in regions outside the core α/β fold. See Silva et al., 2011, Meganucleases and other tools for targeted genome engineering, Curr Gene Ther 11(1):11-27, incorporated by reference.

In some embodiments of the invention, a template sequence is inserted into the genome. In order to introduce nucleotide modifications to genomic DNA, a DNA repair template containing the desired sequence must be present during homology directed repair (HDR). The DNA template is normally transfected into the cell along with the gRNA/Cas9. The length and binding position of each homology arm is dependent on the size of the change being introduced. In the presence of a suitable template, HDR can introduce significant changes at the Cas9 induced double strand break.

Some embodiments of the invention may utilize modified version of a nuclease. Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. Similar to the inactive dCas9 (RuvC- and HNH-), a Cas9 nickase is still able to bind DNA based on gRNA specificity, though nickases will only cut one of the DNA strands. The majority of CRISPR plasmids are derived from *S. pyogenes* and the RuvC domain can be inactivated by a D10A mutation and the HNH domain can be inactivated by an H840A mutation.

A single-strand break, or nick, is normally quickly repaired through the HDR pathway, using the intact complementary DNA strand as the template. However, two proximal, opposite strand nicks introduced by a Cas9 nickase are treated as a double strand break, in what is often referred to as a 'double nick' or 'dual nickase' CRISPR system. A double-nick induced double strain break can be repaired by either NHEJ or HDR depending on the desired effect on the gene target. At these double strain breaks, insertions and deletions are caused by the CRISPR/Cas9 complex. In an aspect of the invention, a deletion is caused by positioning two double strand breaks proximate to one another, thereby causing a fragment of the genome to be deleted.

iii. Targeting Moiety

A nuclease may use the targeting specificity of a guide RNA (gRNA). As discussed below, guide RNAs or single guide RNAs are specifically designed to target a virus genome.

A CRISPR/Cas9 gene editing complex of the invention works optimally with a guide RNA that targets the viral genome. Guide RNA (gRNA) (which includes single guide RNA (sgRNA), crisprRNA (crRNA), transactivating RNA (tracrRNA), any other targeting oligo, or any combination thereof) leads the CRISPR/Cas9 complex to the viral genome in order to cause viral genomic disruption. In an aspect of the invention, CRISPR/Cas9/gRNA complexes are designed to target specific viruses within a cell. It should be appreciated that any virus can be targeted using the composition of the invention. Identification of specific regions of the virus genome aids in development and designing of CRISPR/Cas9/gRNA complexes.

In an aspect of the invention, the CRISPR/Cas9/gRNA complexes are designed to target latent viruses within a cell. Once transfected within a cell, the CRISPR/Cas9/gRNA complexes cause repeated insertions or deletions to render the genome incapacitated, or due to number of insertions or deletions, the probability of repair is significantly reduced.

Figure 1A:
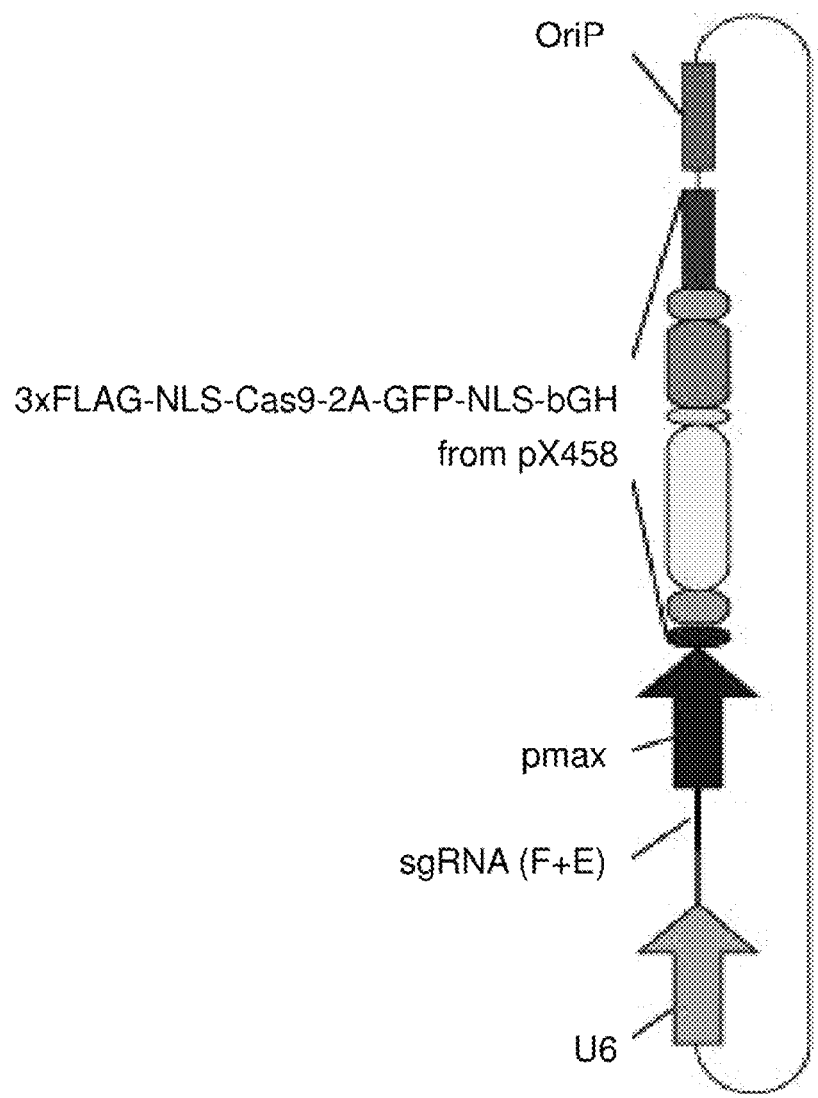
FIGS. 1A-1C represent EBV-targeting CRISPR/Cas9 designs.

As an example, the Epstein-Barr virus (EBV), also called human herpesvirus 4 (HHV-4) is inactivated in cells by a CRISPR/Cas9/gRNA complex of the invention. EBV is a virus of the herpes family, and is one of the most common viruses in humans. The virus is approximately 122 nm to 180 nm in diameter and is composed of a double helix of DNA wrapped in a protein capsid. In this example, the Raji cell line serves as an appropriate in vitro model. The Raji cell line is the first continuous human cell line from hematopoietic origin and cell lines produce an unusual strain of Epstein-Barr virus while being one of the most extensively studied EBV models. To target the EBV genomes in the Raji cells, a CRISPR/Cas9 complex with specificity for EBV is needed. The design of EBV-targeting CRISPR/Cas9 plasmids consisting of a U6 promoter driven chimeric guide RNA (sgRNA) and a ubiquitous promoter driven Cas9 that were obtained from Addgene, Inc. Commercially available guide RNAs and Cas9 nucleases may be used with the present invention. An EGFP marker fused after the Cas9 protein allowed selection of Cas9-positive cells (FIG. 1A).

In an aspect of the invention, guide RNAs are designed, whether or not commercially purchased, to target a specific viral genome. The viral genome is identified and guide RNA to target selected portions of the viral genome are developed and incorporated into the composition of the invention. In an aspect of the invention, a reference genome of a particular strain of the virus is selected for guide RNA design.

Figure 1B:
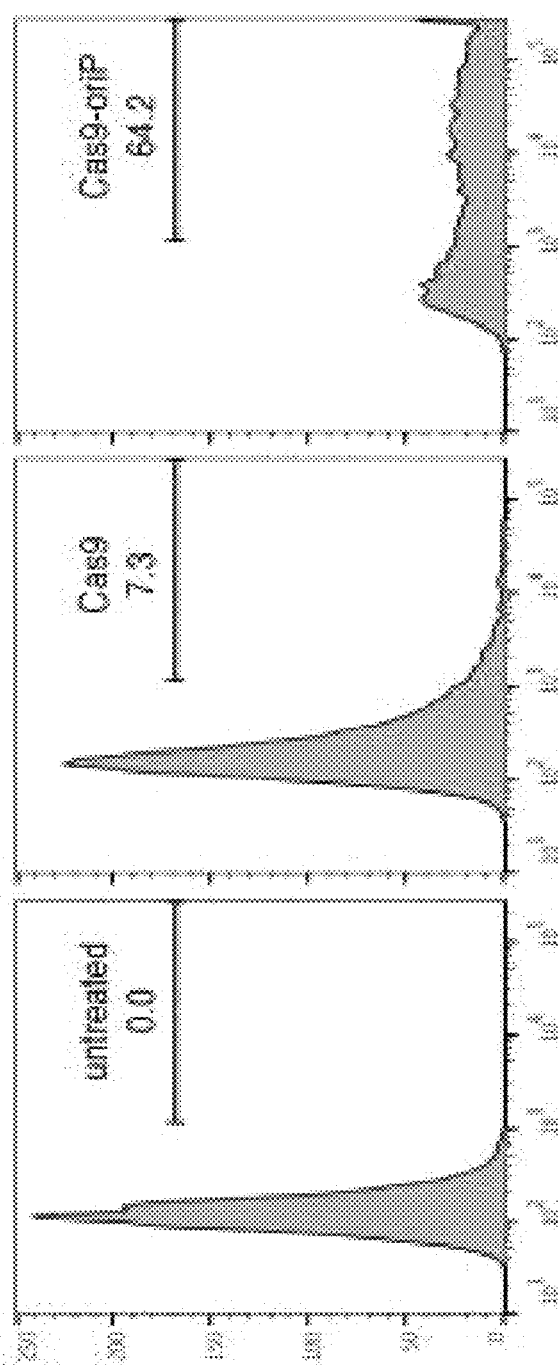
Figure 1C:
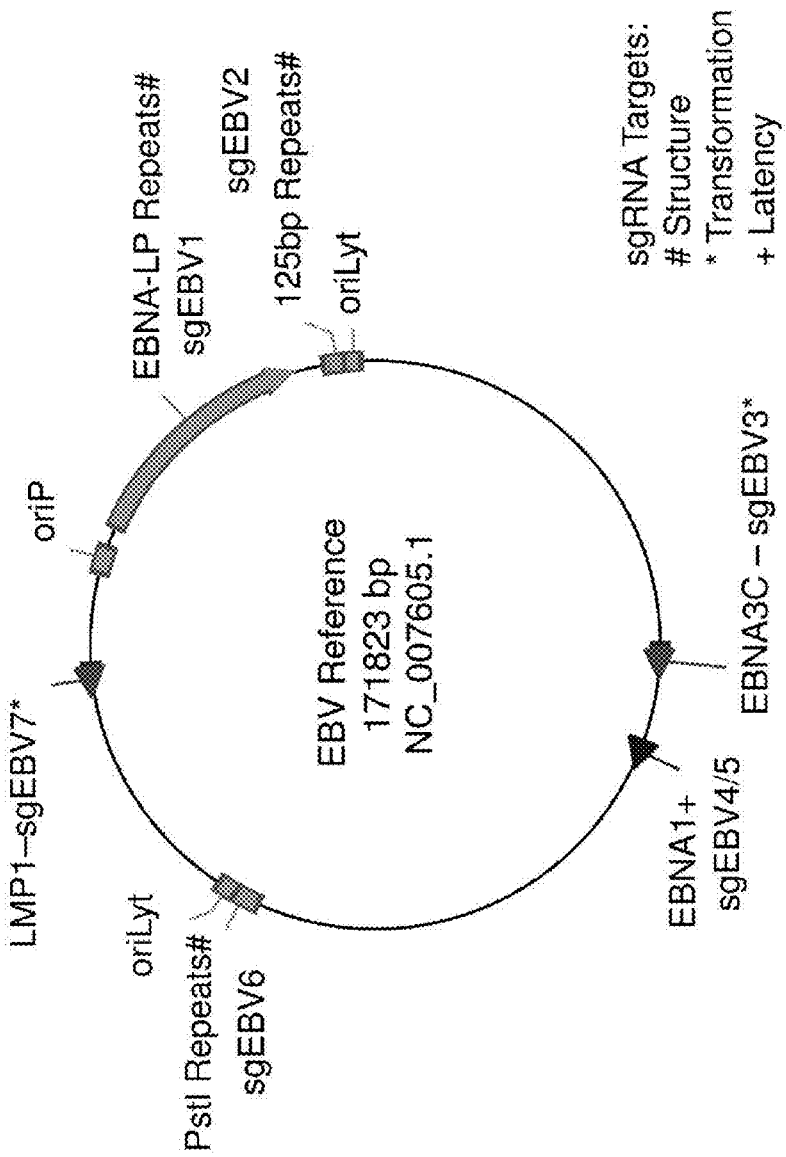

For example, guide RNAs that target the EBV genome are a component of the system in the present example. In relation to EBV, for example, the reference genome from strain B95-8 was used as a design guide. Within a genome of interest, such as EBV, selected regions, or genes are targeted. For example, six regions can be targeted with seven guide RNA designs for different genome editing purposes (FIG. 1C and Table S1). In relation to EBV, EBNA1 is the only nuclear Epstein-Barr virus (EBV) protein expressed in both latent and lytic modes of infection. While EBNA1 is known to play several important roles in latent infection, EBNA1 is crucial for many EBV functions including gene regulation and latent genome replication. Therefore, guide RNAs sgEBV4 and sgEBV5 were selected to target both ends of the EBNA1 coding region in order to excise this whole region of the genome. These "structural" targets enable systematic digestion of the EBV genome into smaller pieces. EBNA3C and LMP1 are essential for host cell transformation, and guide RNAs sgEBV3 and sgEBV7 were designed to target the 5' exons of these two proteins respectively.

iv. Introduce to Cell

Methods of the invention include introducing into a cell a nuclease and a sequence-specific targeting moiety. The nuclease is targeted to viral nucleic acid by means of the sequence-specific targeting moiety where it then cleaves the viral nucleic acid without interfering with a host genome. Any suitable method can be used to deliver the nuclease to the infected cell or tissue. For example, the nuclease or the gene encoding the nuclease may be delivered by injection, orally, or by hydrodynamic delivery. The nuclease or the gene encoding the nuclease may be delivered to systematic circulation or may be delivered or otherwise localized to a specific tissue type. The nuclease or gene encoding the nuclease may be modified or programmed to be active under only certain conditions such as by using a tissue-specific promoter so that the encoded nuclease is preferentially or only transcribed in certain tissue types.

In some embodiments, specific CRISPR/Cas9/gRNA complexes are introduced into a cell. A guide RNA is designed to target at least one category of sequences of the viral genome. In addition to latent infections this invention can also be used to control actively replicating viruses by targeting the viral genome before it is packaged or after it is ejected.

In some embodiments, a cocktail of guide RNAs may be introduced into a cell. The guide RNAs are designed to target numerous categories of sequences of the viral genome. By targeting several areas along the genome, the double strand break at multiple locations fragments the genome, lowering the possibility of repair. Even with repair mechanisms, the large deletions render the virus incapacitated.

In some embodiments, several guide RNAs are added to create a cocktail to target different categories of sequences. For example, two, five, seven or eleven guide RNAs may be present in a CRISPR cocktail targeting three different categories of sequences. However, any number of gRNAs may be introduced into a cocktail to target categories of sequences. In preferred embodiments, the categories of sequences are important for genome structure, host cell transformation, and infection latency, respectively.

In some aspects of the invention, in vitro experiments allow for the determination of the most essential targets within a viral genome. For example, to understand the most essential targets for effective incapacitation of a genome, subsets of guide RNAs are transfected into model cells. Assays can determine which guide RNAs or which cocktail is the most effective at targeting essential categories of sequences.

Figure 2A:
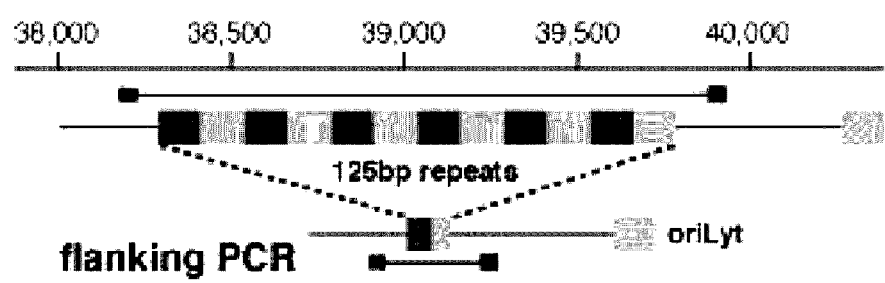
FIGS. 2A-2F represent CRISPR/Cas9 induced large deletions.
Figure 2B:
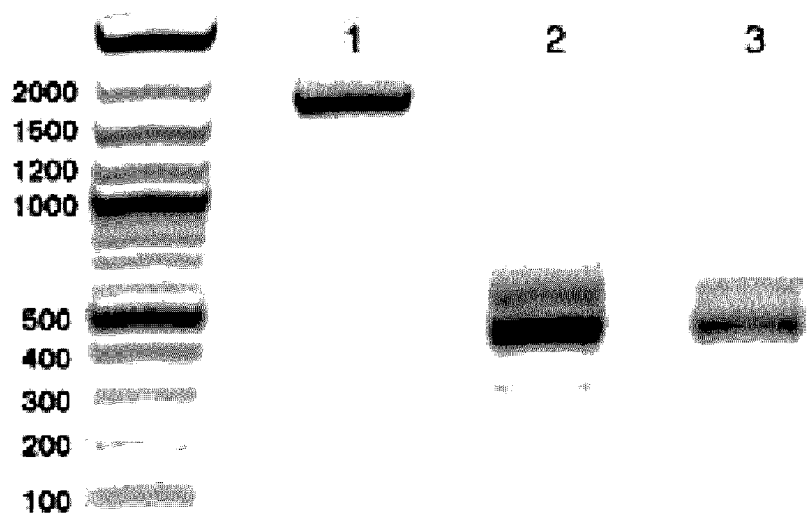

For example, in the case of the EBV genome targeting, seven guide RNAs in the CRISPR cocktail targeted three different categories of sequences which are identified as being important for EBV genome structure, host cell transformation, and infection latency, respectively. To understand the most essential targets for effective EBV treatment, Raji cells were transfected with subsets of guide RNAs. Although sgEBV4/5 reduced the EBV genome by 85%, they could not suppress cell proliferation as effectively as the full cocktail (FIG. 3A). Guide RNAs targeting the structural sequences (sgEBV1/2/6) could stop cell proliferation completely, despite not eliminating the full EBV load (26% decrease). Given the high efficiency of genome editing and the proliferation arrest (FIG. 2), it was suspect that the residual EBV genome signature in sgEBV1/2/6 was not due to intact genomes but to free-floating DNA that has been digested out of the EBV genome, i.e. as a false positive.

Once CRISPR/Cas9/gRNA complexes are constructed, the complexes are introduced into a cell. It should be appreciated that complexes can be introduced into cells in an in vitro model or an in vivo model. In an aspect of the invention, CRISPR/Cas9/gRNA complexes are designed to not leave intact genomes of a virus after transfection and complexes are designed for efficient transfection.

Aspects of the invention allow for CRISPR/Cas9/gRNA to be transfected into cells by various methods, including viral vectors and non-viral vectors. Viral vectors may include retroviruses, lentiviruses, adenoviruses, and adeno-associated viruses. It should be appreciated that any viral vector may be incorporated into the present invention to effectuate delivery of the CRISPR/Cas9/gRNA complex into a cell. Some viral vectors may be more effective than others, depending on the CRISPR/Cas9/gRNA complex designed for digestion or incapacitation. In an aspect of the invention, the vectors contain essential components such as origin of replication, which is necessary for the replication and maintenance of the vector in the host cell.

In an aspect of the invention, viral vectors are used as delivery vectors to deliver the complexes into a cell. Use of viral vectors as delivery vectors are known in the art. See for example U.S. Pub. 2009/0017543 to Wilkes et al., the contents of which are incorporated by reference.

A retrovirus is a single-stranded RNA virus that stores its nucleic acid in the form of an mRNA genome (including the 5' cap and 3' PolyA tail) and targets a host cell as an obligate parasite. In some methods in the art, retroviruses have been used to introduce nucleic acids into a cell. Once inside the host cell cytoplasm the virus uses its own reverse transcriptase enzyme to produce DNA from its RNA genome, the reverse of the usual pattern, thus retro (backwards). This new DNA is then incorporated into the host cell genome by an integrase enzyme, at which point the retroviral DNA is referred to as a provirus. For example, the recombinant retroviruses such as the Moloney murine leukemia virus have the ability to integrate into the host genome in a stable fashion. They contain a reverse transcriptase that allows integration into the host genome. Retroviral vectors can either be replication-competent or replication-defective. In some embodiments of the invention, retroviruses are incorporated to effectuate transfection into a cell, however the CRISPR/Cas9/gRNA complexes are designed to target the viral genome.

In some embodiments of the invention, lentiviruses, which are a subclass of retroviruses, are used as viral vectors. Lentiviruses can be adapted as delivery vehicles (vectors) given their ability to integrate into the genome of non-dividing cells, which is the unique feature of lentiviruses as other retroviruses can infect only dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides.

As opposed to lentiviruses, adenoviral DNA does not integrate into the genome and is not replicated during cell division. Adenovirus and the related AAV would be potential approaches as delivery vectors since they do not integrate into the host's genome. In some aspects of the invention, only the viral genome is to be targeted is effected by the CRISPR/Cas9/gRNA complexes, and not the host's cells. Adeno-associated virus (AAV) is a small virus that infects humans and some other primate species. AAV can infect both dividing and non-dividing cells and may incorporate its genome into that of the host cell. For example, because of its potential use as a gene therapy vector, researchers have created an altered AAV called self-complementary adeno-associated virus (scAAV). Whereas AAV packages a single strand of DNA and requires the process of second-strand synthesis, scAAV packages both strands which anneal together to form double stranded DNA. By skipping second strand synthesis scAAV allows for rapid expression in the cell. Otherwise, scAAV carries many characteristics of its AAV counterpart. Methods of the invention may incorporate herpesvirus, poxvirus, alphavirus, or vaccinia virus as a means of delivery vectors.

In certain embodiments of the invention, non-viral vectors may be used to effectuate transfection. Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam and Lipofectin). Cationic and neutral lipids that are suitable for efficient receptor-recognition lipofection of polynucleotides include those described in U.S. Pat. No. 7,166,298 to Jessee or U.S. Pat. No. 6,890,554 to Jesse, the contents of each of which are incorporated by reference. Delivery can be to cells (e.g. in vitro or ex vivo administration) or target tissues (e.g. in vivo administration).

Synthetic vectors are typically based on cationic lipids or polymers which can complex with negatively charged nucleic acids to form particles with a diameter in the order of 100 nm. The complex protects nucleic acid from degradation by nuclease. Moreover, cellular and local delivery strategies have to deal with the need for internalization, release, and distribution in the proper subcellular compartment. Systemic delivery strategies encounter additional hurdles, for example, strong interaction of cationic delivery vehicles with blood components, uptake by the reticuloendothelial system, kidney filtration, toxicity and targeting ability of the carriers to the cells of interest. Modifying the surfaces of the cationic non-virals can minimize their interaction with blood components, reduce reticuloendothelial system uptake, decrease their toxicity and increase their binding affinity with the target cells. Binding of plasma proteins (also termed opsonization) is the primary mechanism for RES to recognize the circulating nanoparticles. For example, macrophages, such as the Kupffer cells in the liver, recognize the opsonized nanoparticles via the scavenger receptor.

In some embodiments of the invention, non-viral vectors are modified to effectuate targeted delivery and transfection. PEGylation (i.e. modifying the surface with polyethyleneglycol) is the predominant method used to reduce the opsonization and aggregation of non-viral vectors and minimize the clearance by reticuloendothelial system, leading to a prolonged circulation lifetime after intravenous (i.v.) administration. PEGylated nanoparticles are therefore often referred as "stealth" nanoparticles. The nanoparticles that are not rapidly cleared from the circulation will have a chance to encounter infected cells.

However, PEG on the surface can decrease the uptake by target cells and reduce the biological activity. Therefore, to attach targeting ligand to the distal end of the PEGylated component is necessary; the ligand is projected beyond the PEG "shield" to allow binding to receptors on the target cell surface. When cationic liposome is used as gene carrier, the application of neutral helper lipid is helpful for the release of nucleic acid, besides promoting hexagonal phase formation to enable endosomal escape. In some embodiments of the invention, neutral or anionic liposomes are developed for systemic delivery of nucleic acids and obtaining therapeutic effect in experimental animal model. Designing and synthesizing novel cationic lipids and polymers, and covalently or noncovalently binding gene with peptides, targeting ligands, polymers, or environmentally sensitive moieties also attract many attentions for resolving the problems encountered by non-viral vectors. The application of inorganic nanoparticles (for example, metallic nanoparticles, iron oxide, calcium phosphate, magnesium phosphate, manganese phosphate, double hydroxides, carbon nanotubes, and quantum dots) in delivery vectors can be prepared and surface-functionalized in many different ways.

In some embodiments of the invention, targeted controlled-release systems responding to the unique environments of tissues and external stimuli are utilized. Gold nanorods have strong absorption bands in the near-infrared region, and the absorbed light energy is then converted into heat by gold nanorods, the so-called 'photothermal effect'. Because the near-infrared light can penetrate deeply into tissues, the surface of gold nanorod could be modified with nucleic acids for controlled release. When the modified gold nanorods are irradiated by near-infrared light, nucleic acids are released due to thermo-denaturation induced by the photothermal effect. The amount of nucleic acids released is dependent upon the power and exposure time of light irradiation.

In some embodiments of the invention, liposomes are used to effectuate transfection into a cell or tissue. The pharmacology of a liposomal formulation of nucleic acid is largely determined by the extent to which the nucleic acid is encapsulated inside the liposome bilayer. Encapsulated nucleic acid is protected from nuclease degradation, while those merely associated with the surface of the liposome is not protected. Encapsulated nucleic acid shares the extended circulation lifetime and biodistribution of the intact liposome, while those that are surface associated adopt the pharmacology of naked nucleic acid once they disassociate from the liposome.

In some embodiments, the complexes of the invention are encapsulated in a liposome. Unlike small molecule drugs, nucleic acids cannot cross intact lipid bilayers, predominantly due to the large size and hydrophilic nature of the nucleic acid. Therefore, nucleic acids may be entrapped within liposomes with conventional passive loading technologies, such as ethanol drop method (as in SALP), reverse-phase evaporation method, and ethanol dilution method (as in SNALP).

In some embodiments, linear polyethylenimine (L-PEI) is used as a non-viral vector due to its versatility and comparatively high transfection efficiency. L-PEI has been used to efficiently deliver genes in vivo into a wide range of organs such as lung, brain, pancreas, retina, bladder as well as tumor. L-PEI is able to efficiently condense, stabilize and deliver nucleic acids in vitro and in vivo.

Low-intensity ultrasound in combination with microbubbles has recently acquired much attention as a safe method of gene delivery. Ultrasound shows tissue-permeabilizing effect. It is non-invasive and site-specific, and could make it possible to destroy tumor cells after systemic delivery, while leave nontargeted organs unaffected. Ultrasound-mediated microbubbles destruction has been proposed as an innovative method for noninvasive delivering of drugs and nucleic acids to different tissues. Microbubbles are used to carry a drug or gene until a specific area of interest is reached, and then ultrasound is used to burst the microbubbles, causing site-specific delivery of the bioactive materials. Furthermore, the ability of albumin-coated microbubbles to adhere to vascular regions with glycocalix damage or endothelial dysfunction is another possible mechanism to deliver drugs even in the absence of ultrasound. See Tsutsui et al., 2004, The use of microbubbles to target drug delivery, Cardiovasc Ultrasound 2:23, the contents of which are incorporated by reference. In ultrasound-triggered drug delivery, tissue-permeabilizing effect can be potentiated using ultrasound contrast agents, gas-filled microbubbles. The use of microbubbles for delivery of nucleic acids is based on the hypothesis that destruction of DNA-loaded microbubbles by a focused ultrasound beam during their microvascular transit through the target area will result in localized transduction upon disruption of the microbubble shell while sparing non-targeted areas.

Besides ultrasound-mediated delivery, magnetic targeting delivery could be used for delivery. Magnetic nanoparticles are usually entrapped in gene vectors for imaging the delivery of nucleic acid. Nucleic acid carriers can be responsive to both ultrasound and magnetic fields, i.e., magnetic and acoustically active liposheres (MAALs). The basic premise is that therapeutic agents are attached to, or encapsulated within, a magnetic micro- or nanoparticle. These particles may have magnetic cores with a polymer or metal coating which can be functionalized, or may consist of porous polymers that contain magnetic nanoparticles precipitated within the pores. By functionalizing the polymer or metal coating it is possible to attach, for example, cytotoxic drugs for targeted chemotherapy or therapeutic DNA to correct a genetic defect. Once attached, the particle/therapeutic agent complex is injected into the bloodstream, often using a catheter to position the injection site near the target. Magnetic fields, generally from high-field, high-gradient, rare earth magnets are focused over the target site and the forces on the particles as they enter the field allow them to be captured and extravasated at the target.

Synthetic cationic polymer-based nanoparticles (~100 nm diameter) have been developed that offer enhanced transfection efficiency combined with reduced cytotoxicity, as compared to traditional liposomes. The incorporation of distinct layers composed of lipid molecules with varying physical and chemical characteristics into the polymer nanoparticle formulation resulted in improved efficiency through better fusion with cell membrane and entry into the cell, enhanced release of molecules inside the cell, and reduced intracellular degradation of nanoparticle complexes.

In some embodiments, the complexes are conjugated to nano-systems for systemic therapy, such as liposomes, albumin-based particles, PEGylated proteins, biodegradable polymer-drug composites, polymeric micelles, dendrimers, among others. See Davis et al., 2008, Nanotherapeutic particles: an emerging treatment modality for cancer, Nat Rev Drug Discov. 7(9):771-782, incorporated by reference. Long circulating macromolecular carriers such as liposomes, can exploit the enhanced permeability and retention effect for preferential extravasation from tumor vessels. In certain embodiments, the complexes of the invention are conjugated to or encapsulated into a liposome or polymerosome for delivery to a cell. For example, liposomal anthracyclines have achieved highly efficient encapsulation, and include versions with greatly prolonged circulation such as liposomal daunorubicin and pegylated liposomal doxorubicin. See Krishna et al., Carboxymethylcellulose-sodium based transdermal drug delivery system for propranolol, J Pharm Pharmacol. 1996 April; 48(4):367-70.

Liposomal delivery systems provide stable formulation, provide improved pharmacokinetics, and a degree of 'passive' or 'physiological' targeting to tissues. Encapsulation of hydrophilic and hydrophobic materials, such as potential chemotherapy agents, are known. See for example U.S. Pat. No. 5,466,468 to Schneider, which discloses parenterally administrable liposome formulation comprising synthetic lipids; U.S. Pat. No. 5,580,571, to Hostetler et al. which discloses nucleoside analogues conjugated to phospholipids; U.S. Pat. No. 5,626,869 to Nyqvist, which discloses pharmaceutical compositions wherein the pharmaceutically active compound is heparin or a fragment thereof contained in a defined lipid system comprising at least one amphiphatic and polar lipid component and at least one nonpolar lipid component.

Liposomes and polymerosomes can contain a plurality of solutions and compounds. In certain embodiments, the complexes of the invention are coupled to or encapsulated in polymersomes. As a class of artificial vesicles, polymersomes are tiny hollow spheres that enclose a solution, made using amphiphilic synthetic block copolymers to form the vesicle membrane. Common polymersomes contain an aqueous solution in their core and are useful for encapsulating and protecting sensitive molecules, such as drugs, enzymes, other proteins and peptides, and DNA and RNA fragments. The polymersome membrane provides a physical barrier that isolates the encapsulated material from external materials, such as those found in biological systems. Polymerosomes can be generated from double emulsions by known techniques, see Lorenceau et al., 2005, Generation of Polymerosomes from Double-Emulsions, Langmuir 21(20): 9183-6, incorporated by reference.

Some embodiments of the invention provide for a gene gun or a biolistic particle delivery system. A gene gun is a device for injecting cells with genetic information, where the payload may be an elemental particle of a heavy metal coated with plasmid DNA. This technique may also be referred to as bioballistics or biolistics. Gene guns have also been used to deliver DNA vaccines. The gene gun is able to transfect cells with a wide variety of organic and non-organic species, such as DNA plasmids, fluorescent proteins, dyes, etc.

Aspects of the invention provide for numerous uses of delivery vectors. Selection of the delivery vector is based upon the cell or tissue targeted and the specific makeup of the CRISPR/Cas9/gRNA. For example, in the EBV example discussed above, since lymphocytes are known for being resistant to lipofection, nucleofection (a combination of electrical parameters generated by a device called Nucleofector, with cell-type specific reagents to transfer a substrate directly into the cell nucleus and the cytoplasm) was necessitated for DNA delivery into the Raji cells. The Lonza pmax promoter drives Cas9 expression as it offered strong expression within Raji cells. 24 hours after nucleofection, obvious EGFP signals were observed from a small proportion of cells through fluorescent microscopy. The EGFP-positive cell population decreased dramatically, however, <10% transfection efficiency 48 hours after nucleofection was measured (FIG. 1B). A CRISPR plasmid that included the EBV origin of replication sequence, oriP yielded a transfection efficiency >60% (FIG. 1B).

Aspects of the invention utilize the CRISPR/Cas9/gRNA complexes for the targeted delivery. Common known pathways include transdermal, transmucal, nasal, ocular and pulmonary routes. Drug delivery systems may include liposomes, proliposomes, microspheres, gels, prodrugs, cyclodextrins, etc. Aspects of the invention utilize nanoparticles composed of biodegradable polymers to be transferred into an aerosol for targeting of specific sites or cell populations in the lung, providing for the release of the drug in a predetermined manner and degradation within an acceptable period of time. Controlled-release technology (CRT), such as transdermal and transmucosal controlled-release delivery systems, nasal and buccal aerosol sprays, drug-impregnated lozenges, encapsulated cells, oral soft gels, iontophoretic devices to administer drugs through skin, and a variety of programmable, implanted drug-delivery devices are used in conjunction with the complexes of the invention of accomplishing targeted and controlled delivery.

v. Cut Viral Nucleic Acid

Once inside the cell, the CRISPR/Cas9/gRNA complexes target the viral genome. In an aspect of the invention, the complexes are targeted to viral genomes. In addition to latent infections this invention can also be used to control actively replicating viruses by targeting the viral genome before it is packaged or after it is ejected. In some embodiments, methods and compositions of the invention use a nuclease such as Cas9 to target latent viral genomes, thereby reducing the chances of proliferation. The nuclease may form a complex with a gRNA (e.g., crRNA+tracrRNA or sgRNA). The complex cuts the viral nucleic acid in a targeted fashion to incapacitate the viral genome. As discussed above, the Cas9 endonuclease causes a double strand break in the viral genome. By targeted several locations along the viral genome and causing not a single strand break, but a double strand break, the genome is effectively cut a several locations along the genome. In a preferred embodiment, the double strand breaks are designed so that small deletions are caused, or small fragments are removed from the genome so that even if natural repair mechanisms join the genome together, the genome is render incapacitated.

After introduction into a cell, the CRISPR/Cas9/gRNA complexes act on the viral genome, genes, transcripts, or other viral nucleic acid. The double-strand DNA breaks generated by CRISPR are repaired with small deletions. These deletions will disrupt the protein coding and hence create knockout effects.

The nuclease, or a gene encoding the nuclease, may be delivered into an infected cell by transfection. For example, the infected cell can be transfected with DNA that encodes Cas9 and gRNA (on a single piece or separate pieces). The gRNAs are designed to localize the Cas9 endonuclease at one or several locations along the viral genome. The Cas9 endonuclease causes double strand breaks in the genome, causing small fragments to be deleted from the viral genome. Even with repair mechanisms, the deletions render the viral genome incapacitated.

vi. Host Genome

It will be appreciated that method and compositions of the invention can be used to target viral nucleic acid without interfering with host genetic material. Methods and compositions of the invention employ a targeting moiety such as a guide RNA that has a sequence that hybridizes to a target within the viral sequence. Methods and compositions of the invention may further use a targeted nuclease such as the cas9 enzyme, or a vector encoding such a nuclease, which uses the gRNA to bind exclusively to the viral genome and make double stranded cuts, thereby removing the viral sequence from the host.

Where the targeting moiety includes a guide RNA, the sequence for the gRNA, or the guide sequence, can be determined by examination of the viral sequence to find regions of about 20 nucleotides that are adjacent to a protospacer adjacent motif (PAM) and that do not also appear in the host genome adjacent to the protospacer motif. Preferably a guide sequence that satisfies certain similarity criteria (e.g., at least 60% identical with identity biased toward regions closer to the PAM) so that a gRNA/cas9 complex made according to the guide sequence will bind to and digest specified features or targets in the viral sequence without interfering with the host genome. Preferably, the guide RNA corresponds to a nucleotide string next to a protospacer adjacent motif (PAM) (e.g., NGG, where N is any nucleotide) in the viral sequence. Preferably, the host genome lacks any region that (1) matches the nucleotide string according to a predetermined similarity criteria and (2) is also adjacent to the PAM. The predetermined similarity criteria may include, for example, a requirement of at least 12 matching nucleotides within 20 nucleotides 5' to the PAM and may also include a requirement of at least 7 matching nucleotides within 10 nucleotides 5' to the PAM. An annotated viral genome (e.g., from GenBank) may be used to identify features of the viral sequence and finding the nucleotide string next to a protospacer adjacent motif (PAM) in the viral sequence within a selected feature (e.g., a viral replication origin, a terminal repeat, a replication factor binding site, a promoter, a coding sequence, or a repetitive region) of the viral sequence. The viral sequence and the annotations may be obtained from a genome database.

Where multiple candidate gRNA targets are found in the viral genome, selection of the sequence to be the template for the guide RNA may favor the candidate target closest to, or at the 5' most end of, a targeted feature as the guide sequence. The selection may preferentially favor sequences with neutral (e.g., 40% to 60%) GC content. Additional background regarding the RNA-directed targeting by endonuclease is discussed in U.S. Pub. 2015/0050699; U.S. Pub. 20140356958; U.S. Pub. 2014/0349400; U.S. Pub. 2014/0342457; U.S. Pub. 2014/0295556; and U.S. Pub. 2014/0273037, the contents of each of which are incorporated by reference for all purposes. Due to the existence of human genomes background in the infected cells, a set of steps are provided to ensure high efficiency against the viral genome and low off-target effect on the human genome. Those steps may include (1) target selection within viral genome, (2) avoiding PAM+target sequence in host genome, (3) methodologically selecting viral target that is conserved across strains, (4) selecting target with appropriate GC content, (5) control of nuclease expression in cells, (6) vector design, (7) validation assay, others and various combinations thereof. A targeting moiety (such as a guide RNA) preferably binds to targets within certain categories such as (i) latency related targets, (ii) infection and symptom related targets, and (iii) structure related targets.

A first category of targets for gRNA includes latency-related targets. The viral genome requires certain features in order to maintain the latency. These features include, but not limited to, master transcription regulators, latency-specific promoters, signaling proteins communicating with the host cells, etc. If the host cells are dividing during latency, the viral genome requires a replication system to maintain genome copy level. Viral replication origin, terminal repeats, and replication factors binding to the replication origin are great targets. Once the functions of these features are disrupted, the viruses may reactivate, which can be treated by conventional antiviral therapies.

A second category of targets for gRNA includes infection-related and symptom-related targets. Virus produces various molecules to facilitate infection. Once gained entrance to the host cells, the virus may start lytic cycle, which can cause cell death and tissue damage (HBV). In certain cases, such as HPV16, cell products (E6 and E7 proteins) can transform the host cells and cause cancers. Disrupting the key genome sequences (promoters, coding sequences, etc) producing these molecules can prevent further infection, and/or relieve symptoms, if not curing the disease.

A third category of targets for gRNA includes structure-related targets. Viral genome may contain repetitive regions to support genome integration, replication, or other functions. Targeting repetitive regions can break the viral genome into multiple pieces, which physically destroys the genome.

Where the nuclease is a cas protein, the targeting moiety is a guide RNA. Each cas protein requires a specific PAM next to the targeted sequence (not in the guide RNA). This is the same as for human genome editing. The current understanding the guide RNA/nuclease complex binds to PAM first, then searches for homology between guide RNA and target genome. Sternberg et al., 2014, DNA interrogation by the CRISPR RNA-guided endonuclease Cas9, Nature 507(7490):62-67. Once recognized, the DNA is digested 3-nt upstream of PAM. These results suggest that off-target digestion requires PAM in the host DNA, as well as high affinity between guide RNA and host genome right before PAM.

It may be preferable to use a targeting moiety that targets portions of the viral genome that are highly conserved. Viral genomes are much more variable than human genomes. In order to target different strains, the guide RNA will preferably target conserved regions. As PAM is important to initial sequence recognition, it is also essential to have PAM in the conserved region.

In a preferred embodiment, methods of the invention are used to deliver a nucleic acid to cells. The nucleic acid delivered to the cells may include a gRNA having the determined guide sequence or the nucleic acid may include a vector, such as a plasmid, that encodes an enzyme that will act against the target genetic material. Expression of that enzyme allows it to degrade or otherwise interfere with the target genetic material. The enzyme may be a nuclease such as the Cas9 endonuclease and the nucleic acid may also encode one or more gRNA having the determined guide sequence.

The gRNA targets the nuclease to the target genetic material. Where the target genetic material includes the genome of a virus, gRNAs complementary to parts of that genome can guide the degradation of that genome by the nuclease, thereby preventing any further replication or even removing any intact viral genome from the cells entirely. By these means, latent viral infections can be targeted for eradication.

The host cells may grow at different rate, based on the specific cell type. High nuclease expression is necessary for fast replicating cells, whereas low expression help avoiding off-target cutting in non-infected cells. Control of nuclease expression can be achieved through several aspects. If the nuclease is expressed from a vector, having the viral replication origin in the vector can increase the vector copy number dramatically, only in the infected cells. Each promoter has different activities in different tissues. Gene transcription can be tuned by choosing different promoters. Transcript and protein stability can also be tuned by incorporating stabilizing or destabilizing (ubiquitin targeting sequence, etc) motif into the sequence.

Specific promoters may be used for the gRNA sequence, the nuclease (e.g., cas9), other elements, or combinations thereof. For example, in some embodiments, the gRNA is driven by a U6 promoter. A vector may be designed that includes a promoter for protein expression (e.g., using a promoter as described in the vector sold under the trademark PMAXCLONING by Lonza Group Ltd (Basel, Switzerland). A vector may be a plasmid (e.g., created by synthesis instrument 255 and recombinant DNA lab equipment). In certain embodiments, the plasmid includes a U6 promoter driven gRNA or chimeric guide RNA (sgRNA) and a ubiquitous promoter-driven cas9. Optionally, the vector may include a marker such as EGFP fused after the cas9 protein to allow for later selection of cas9+ cells. It is recognized that cas9 can use a gRNA (similar to the CRISPR RNA (crRNA) of the original bacterial system) with a complementary trans-activating crRNA (tracrRNA) to target viral sequences complementary to the gRNA. It has also been shown that cas9 can be programmed with a single RNA molecule, a chimera of the gRNA and tracrRNA. The single guide RNA (sgRNA) can be encoded in a plasmid and transcription of the sgRNA can provide the programming of cas9 and the function of the tracrRNA. See Jinek, 2012, A programmable dual-RNA-guided DNA endonuclease in adaptive bacterial immunity, Science 337:816-821 and especially FIG. 5A therein for background.

Using the above principles, methods and compositions of the invention may be used to target viral nucleic acid in an infected host without adversely influencing the host genome.

For additional background see Hsu, 2013, DNA targeting specificity of RNA-guided Cas9 nucleases, Nature Biotechnology 31(9):827-832; and Jinek, 2012, A programmable dual-RNA-guided DNA endonuclease in adaptive bacterial immunity, Science 337:816-821, the contents of each of which are incorporated by reference. Since the targeted locations are selected to be within certain categories such as (i) latency related targets, (ii) infection and symptom related targets, or (iii) structure related targets, cleavage of those sequences inactivates the virus and removes it from the host. Since the targeting RNA (the gRNA or sgRNA) is designed to satisfy according to similarity criteria that matches the target in the viral genetic sequence without any off-target matching the host genome, the latent viral genetic material is removed from the host without any interference with the host genome.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Targeting EBV

Burkitt's lymphoma cell lines Raji, Namalwa, and DG-75 were obtained from ATCC and cultured in RPMI 1640 supplemented with 10% FBS and PSA, following ATCC recommendation. Human primary lung fibroblast IMR-90 was obtained from Coriell and cultured in Advanced DMEM/F-12 supplemented with 10% FBS and PSA.

Plasmids consisting of a U6 promoter driven chimeric guide RNA (sgRNA) and a ubiquitous promoter driven Cas9 were obtained from addgene, as described by Cong L et al. (2013) Multiplex Genome Engineering Using CRISPR/Cas Systems. Science 339:819-823. An EGFP marker fused after the Cas9 protein allowed selection of Cas9-positive cells (FIG. 1A). We adapted a modified chimeric guide RNA design for more efficient Pol-III transcription and more stable stem-loop structure (Chen B et al. (2013) Dynamic Imaging of Genomic Loci in Living Human Cells by an Optimized CRISPR/Cas System. Cell 155:1479-1491).

We obtained pX458 from Addgene, Inc. A modified CMV promoter with a synthetic intron (pmax) was PCR amplified from Lonza control plasmid pmax-GFP. A modified guide RNA sgRNA(F+E) was ordered from IDT. EBV replication origin oriP was PCR amplified from B95-8 transformed lymphoblastoid cell line GM12891. We used standard cloning protocols to clone pmax, sgRNA(F+E) and oriP to pX458, to replace the original CAG promoter, sgRNA and f1 origin. We designed EBV sgRNA based on the B95-8 reference, and ordered DNA oligos from IDT. The original sgRNA place holder in pX458 serves as the negative control.

Lymphocytes are known for being resistant to lipofection, and therefore we used nucleofection for DNA delivery into Raji cells. We chose the Lonza pmax promoter to drive Cas9 expression as it offered strong expression within Raji cells. We used the Lonza Nucleofector II for DNA delivery. 5 million Raji or DG-75 cells were transfected with 5 ug plasmids in each 100-ul reaction. Cell line Kit V and program M-013 were used following Lonza recommendation. For IMR-90, 1 million cells were transfected with 5 ug plasmids in 100 ul Solution V, with program T-030 or X-005. 24 hours after nucleofection, we observed obvious EGFP signals from a small proportion of cells through fluorescent microscopy. The EGFP-positive cell population decreased dramatically after that, however, and we measured <10% transfection efficiency 48 hours after nucleofection (FIG. 1B). We attributed this transfection efficiency decrease to the plasmid dilution with cell division. To actively maintain the plasmid level within the host cells, we redesigned the CRISPR plasmid to include the EBV origin of replication sequence, oriP. With active plasmid replication inside the cells, the transfection efficiency rose to >60% (FIG. 1B).

To design guide RNA targeting the EBV genome, we relied on the EBV reference genome from strain B95-8. We targeted six regions with seven guide RNA designs for different genome editing purposes (FIG. 1C and Table S1).

TABLE S1

Guide RNA target sequences sgEBV1
(SEQ ID NO: 1)
GCCCTGGACCAACCCGGCCC sgEBV2
(SEQ ID NO: 2)
GGCCGCTGCCCCGCTCCGGG sgEBB3
(SEQ ID NO: 3)
GGAAGACAATGTGCCGCCA sgEBV4
(SEQ ID NO: 4)
TCTGGACCAGAAGGCTCCGG sgEBV5
(SEQ ID NO: 5)
GCTGCCGCGGAGGGTGATGA sgEBV6
(SEQ ID NO: 6)
GGTGGCCCACCGGGTCCGCT sgEBV7
(SEQ ID NO: 7)
GTCCTCGAGGGGGCCGTCGC EBNA1 is crucial for many EBV functions including gene regulation and latent genome replication. We targeted guide RNA sgEBV4 and sgEBV5 to both ends of the EBNA1 coding region in order to excise this whole region of the genome. Guide RNAs sgEBV1, 2 and 6 fall in repeat regions, so that the success rate of at least one CRISPR cut is multiplied. These "structural" targets enable systematic digestion of the EBV genome into smaller pieces. EBNA3C and LMP1 are essential for host cell transformation, and we designed guide RNAs sgEBV3 and sgEBV7 to target the 5' exons of these two proteins respectively.

Figure 5:
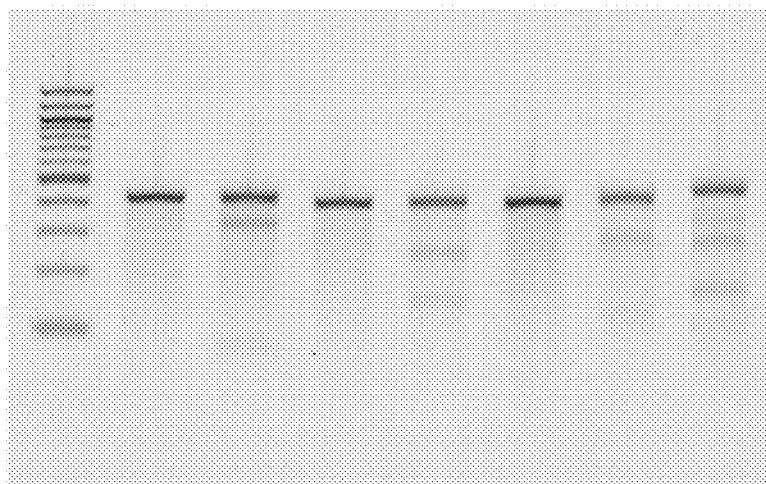
FIG. 5 represents SURVEYOR assay of EBV CRISPR. Lane 1: NEB 100 bp ladder; Lane 2: sgEBV1 control; Lane 3: sgEBV1; Lane 4: sgEBV5 control; Lane 5: sgEBV5; Lane 6: sgEBV7 control; Lane 7: sgEBV7; Lane 8: sgEBV4.

EBV Genome Editing. The double-strand DNA breaks generated by CRISPR are repaired with small deletions. These deletions will disrupt the protein coding and hence create knockout effects. SURVEYOR assays confirmed efficient editing of individual sites (FIG. 5). Beyond the independent small deletions induced by each guide RNA, large deletions between targeting sites can systematically destroy the EBV genome. Guide RNA sgEBV2 targets a region with twelve 125-bp repeat units (FIG. 2A). PCR amplicon of the whole repeat region gave a ~1.8-kb band (FIG. 2B). After 5 or 7 days of sgEBV2 transfection, we obtained ~0.4-kb bands from the same PCR amplification (FIG. 2B). The ~1.4-kb deletion is the expected product of repair ligation between cuts in the first and the last repeat unit (FIG. 2A).

DNA sequences flanking sgRNA targets were PCR amplified with Phusion DNA polymerase. SURVEYOR assays were performed following manufacturer's instruction. DNA amplicons with large deletions were TOPO cloned and single colonies were used for Sanger sequencing. EBV load was measured with Taqman digital PCR on Fluidigm BioMark. A Taqman assay targeting a conserved human locus was used for human DNA normalization. 1 ng of single-cell whole-genome amplification products from Fluidigm C1 were used for EBV quantitative PCR.

Figure 2C:
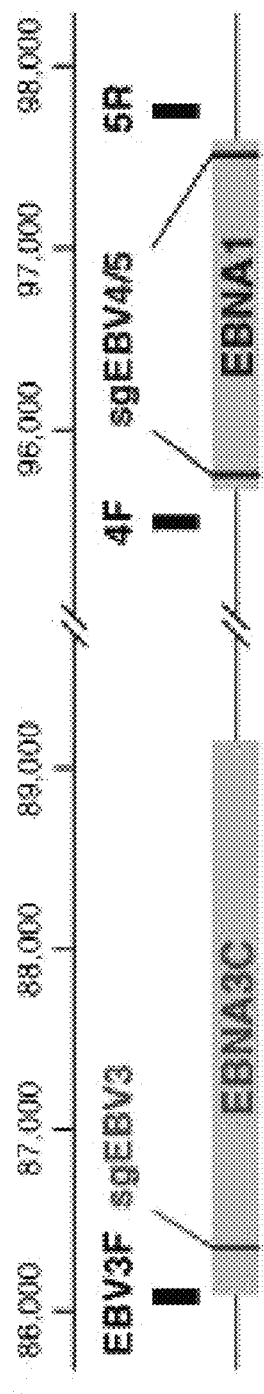
Figure 2D:
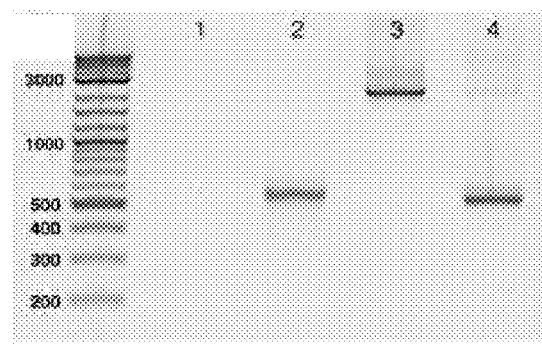
Figure 2E:
Figure 2F:
Figure 3A:
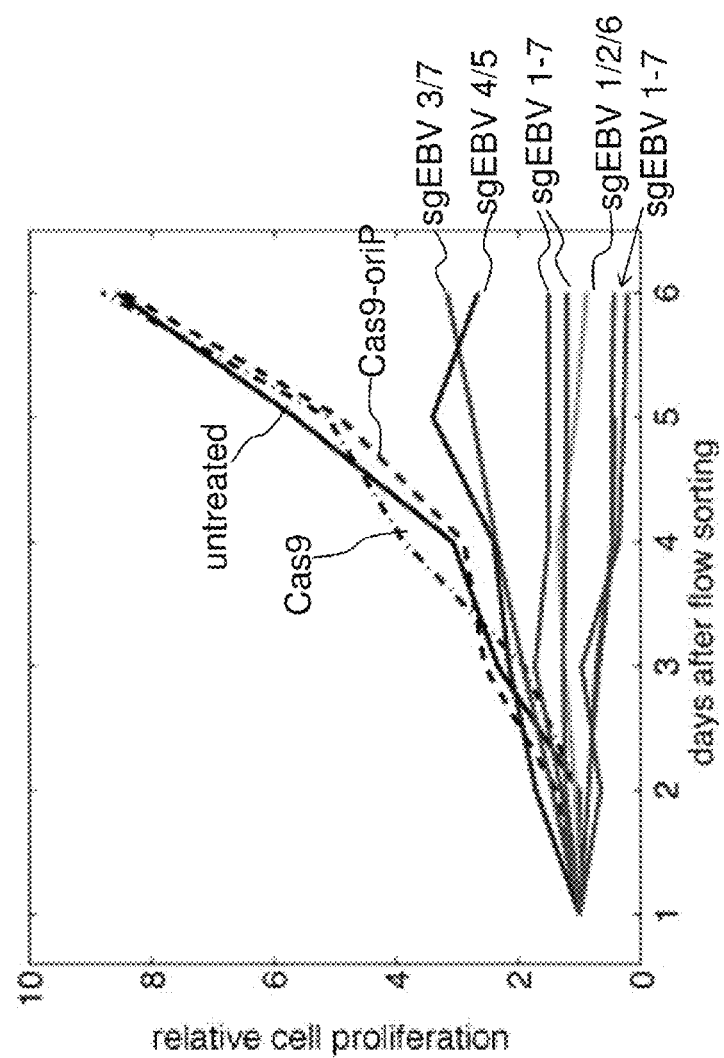
FIGS. 3A-3M represent cell proliferation arrest with EBV genome destruction.

We further demonstrated that it is possible to delete regions between unique targets (FIG. 2C). Six days after sgEBV4-5 transfection, PCR amplification of the whole flanking region (with primers EBV4F and 5R) returned a shorter amplicon, together with a much fainter band of the expected 2 kb (FIG. 2D). Sanger sequencing of amplicon clones confirmed the direct connection of the two expected cutting sites (FIG. 2F). A similar experiment with sgEBV3-5 also returned an even larger deletion, from EBNA3C to EBNA1 (FIG. 2D-E).

Additional information such as primer design is shown in Wang and Quake, 2014, RNA-guided endonuclease provides a therapeutic strategy to cure latent herpesviridae infection, PNAS 111(36):13157-13162 and in the Supporting Information to that article published online at the PNAS website, and the contents of both of those documents are incorporated by reference for all purposes.

Figure 3B:
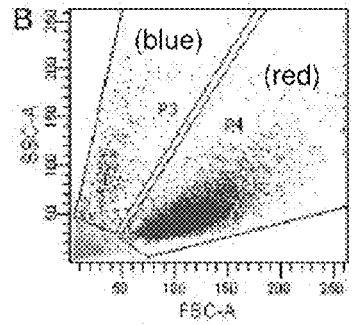
Figure 3E:
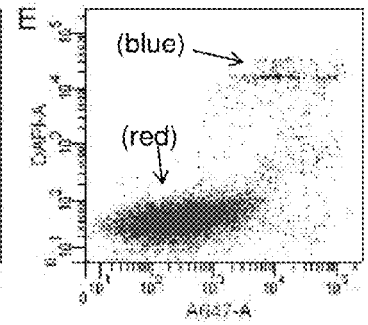
Figure 3C:
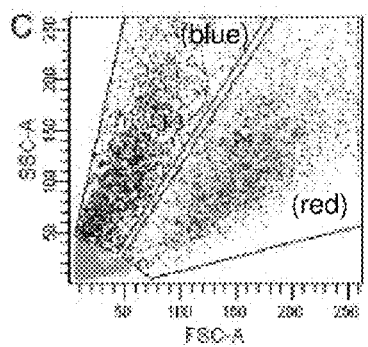
Figure 3F:
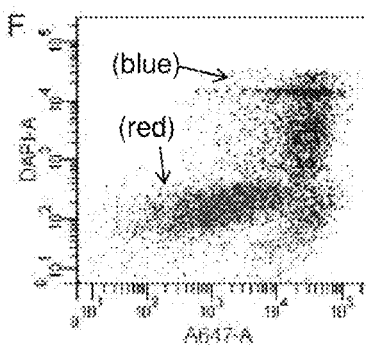
Figure 3D:
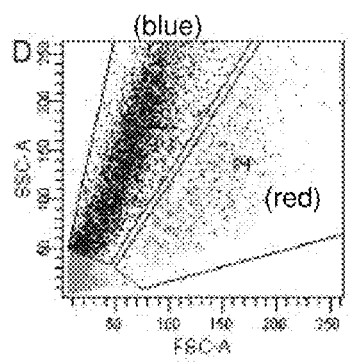
Figure 3G:
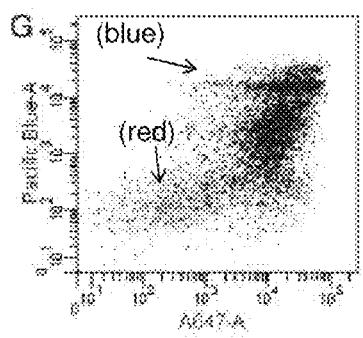
Figure 6:
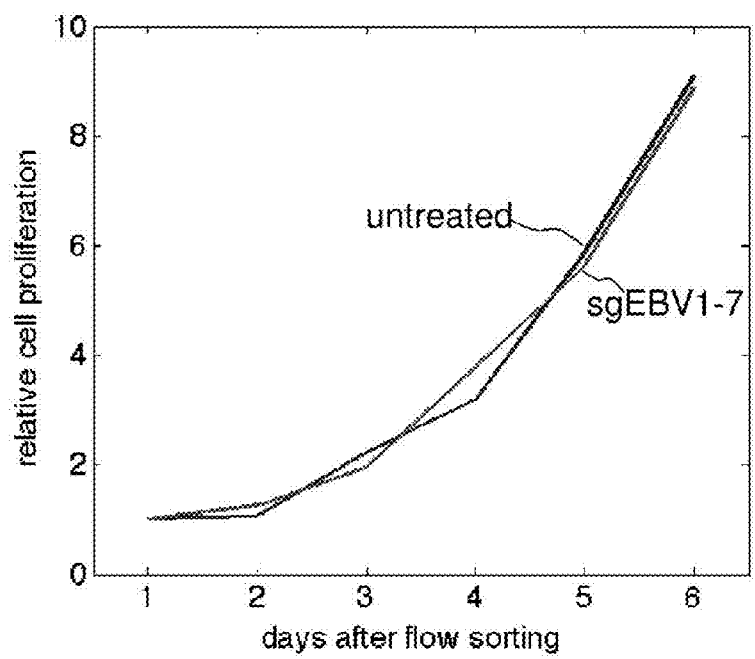
FIG. 6 shows CRISPR cytotoxicity test with EBV-negative Burkitt's lymphoma DG-75.
Figure 7:
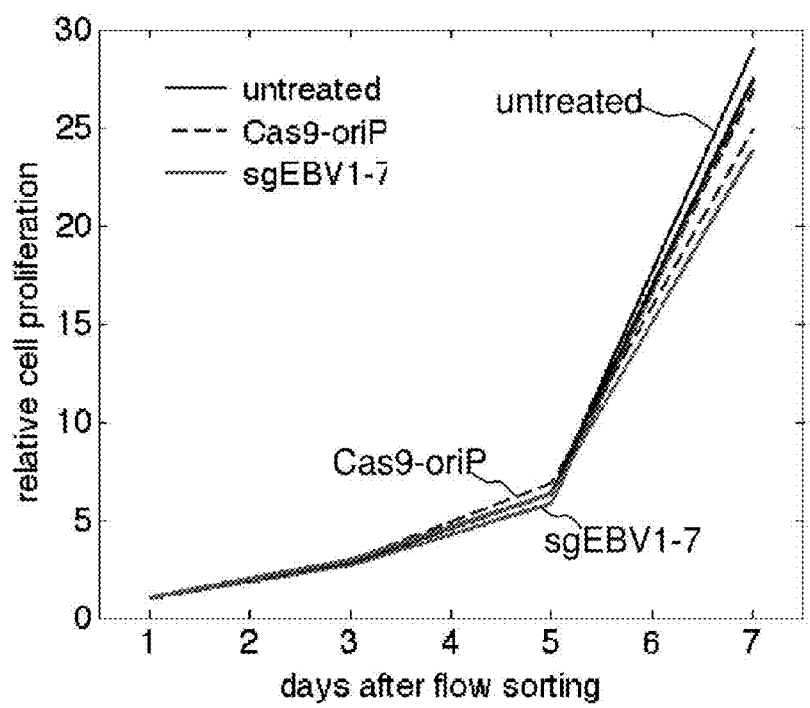
FIG. 7 represents CRISPR cytotoxicity test with primary human lung fibroblast IMR-90.

Cell Proliferation Arrest With EBV Genome Destruction. Two days after CRISPR transfection, we flow sorted EGFP-positive cells for further culture and counted the live cells daily. As expected, cells treated with Cas9 plasmids which lacked oriP or sgEBV lost EGFP expression within a few days and proliferated with a rate similar rate to the untreated control group (FIG. 3A). Plasmids with Cas9-oriP and a scrambled guide RNA maintained EGFP expression after 8 days, but did not reduce the cell proliferation rate. Treatment with the mixed cocktail sgEBV1-7 resulted in no measurable cell proliferation and the total cell count either remained constant or decreased (FIG. 3A). Flow cytometry scattering signals clearly revealed alterations in the cell morphology after sgEBV1-7 treatment, as the majority of the cells shrank in size with increasing granulation (FIG. 3B-D, population P4 to P3 shift). Cells in population P3 also demonstrated compromised membrane permeability by DAPI staining (FIG. 3E-G). To rule out the possibility of CRISPR cytotoxicity, especially with multiple guide RNAs, we performed the same treatment on two other samples: the EBV-negative Burkitt's lymphoma cell line DG-75 (FIG. 6) and primary human lung fibroblast IMR90 (FIG. 7). Eight and nine days after transfection the cell proliferation rates did not change from the untreated control groups, suggesting neglectable cytotoxicity.

Figure 3H:
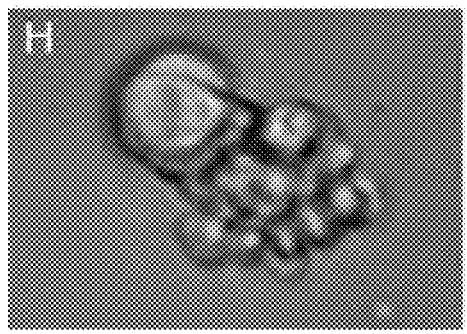
Figure 3I:
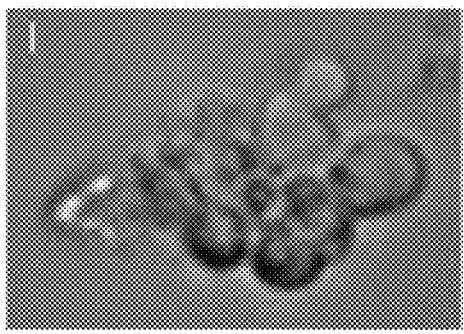
Figure 3J:
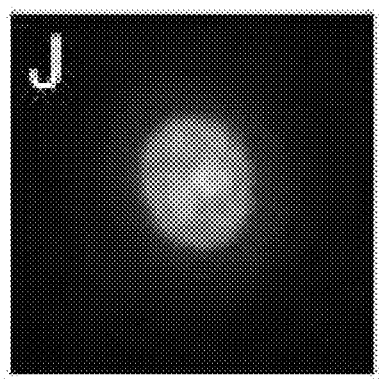
Figure 3K:
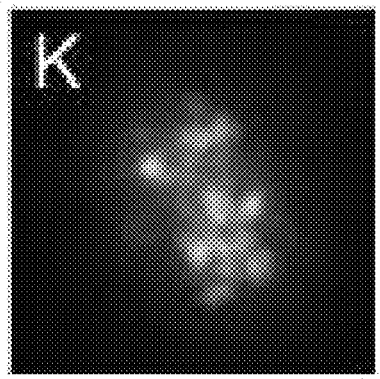
Figure 3L:
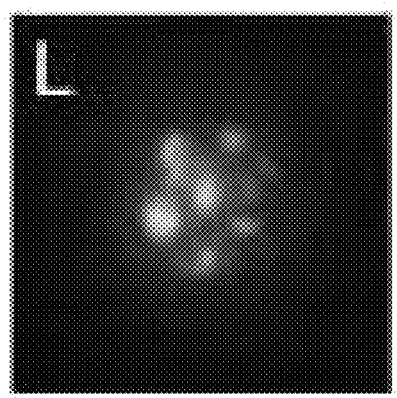
Figure 3M:
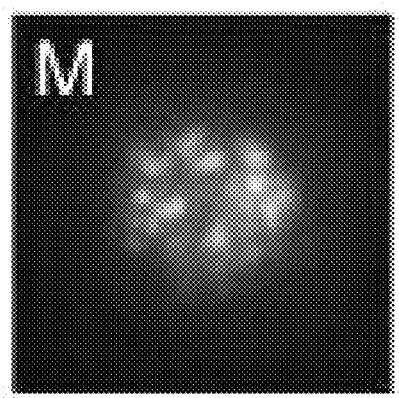

Previous studies have attributed the EBV tumorigenic ability to its interruption of host cell apoptosis (Ruf I K et al. (1999) Epstein-Barr Virus Regulates c-MYC, Apoptosis, and Tumorigenicity in Burkitt Lymphoma. Molecular and Cellular Biology 19:1651-1660). Suppressing EBV activities may therefore restore the apoptosis process, which could explain the cell death observed in our experiment Annexin V staining revealed a distinct subpopulation of cells with intact cell membrane but exposed phosphatidylserine, suggesting cell death through apoptosis (FIG. 3E-G). Bright field microscopy showed obvious apoptotic cell morphology (FIG. 3H-I) and fluorescent staining demonstrated drastic DNA fragmentation (FIG. 3J-M). Altogether this evidence suggests restoration of the normal host cell apoptosis pathway after EBV genome destruction.

Figure 4A:
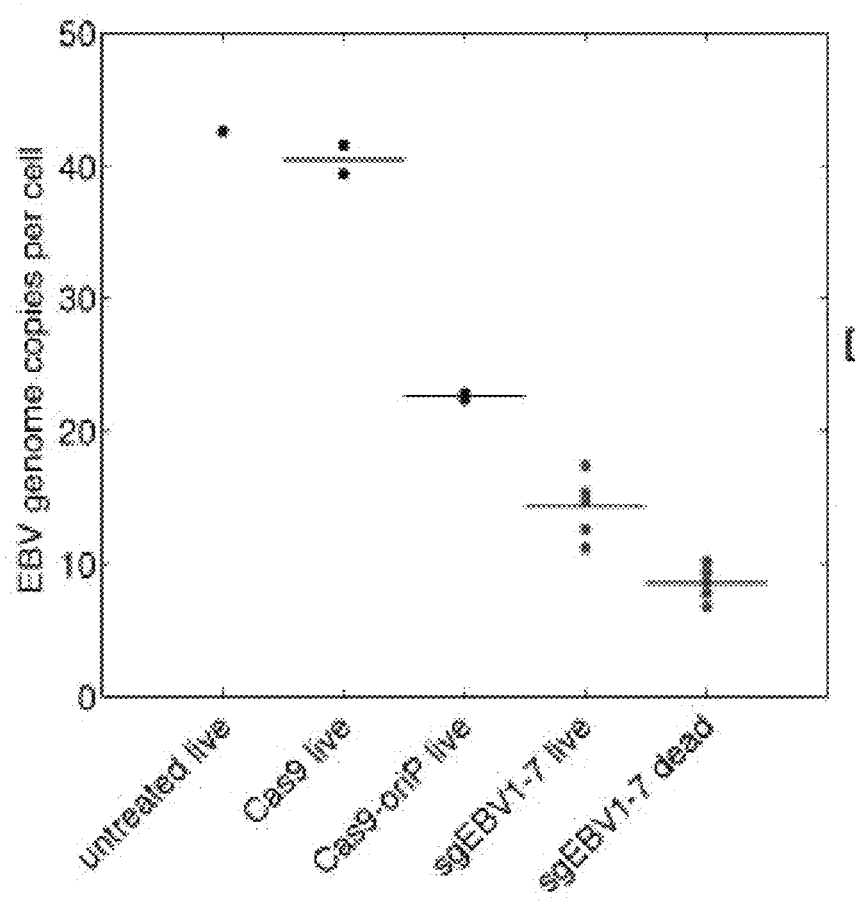
FIGS. 4A-4E represent EBV load quantitation after CRISPR treatment.

Complete Clearance Of EBV In A Subpopulation. To study the potential connection between cell proliferation arrest and EBV genome editing, we quantified the EBV load in different samples with digital PCR targeting EBNA1. Another Taqman assay targeting a conserved human somatic locus served as the internal control for human DNA normalization. On average, each untreated Raji cell has 42 copies of EBV genome (FIG. 4A). Cells treated with a Cas9 plasmid that lacked oriP or sgEBV did not have an obvious difference in EBV load difference from the untreated control. Cells treated with a Cas9-plasmid with oriP but no sgEBV had an EBV load that was reduced by ~50%. In conjunction with the prior observation that cells from this experiment did not show any difference in proliferation rate, we interpret this as likely due to competition for EBNA1 binding during plasmid replication. The addition of the guide RNA cocktail sgEBV1-7 to the transfection dramatically reduced the EBV load. Both the live and dead cells have >60% EBV decrease comparing to the untreated control.

Figure 4B:
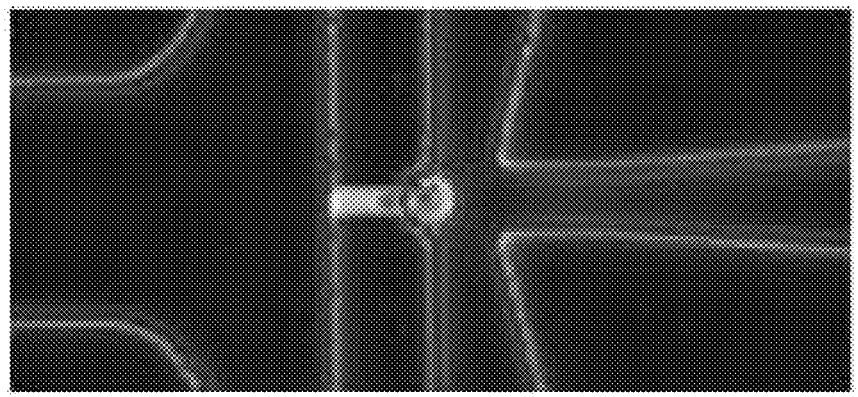
Figure 4C:
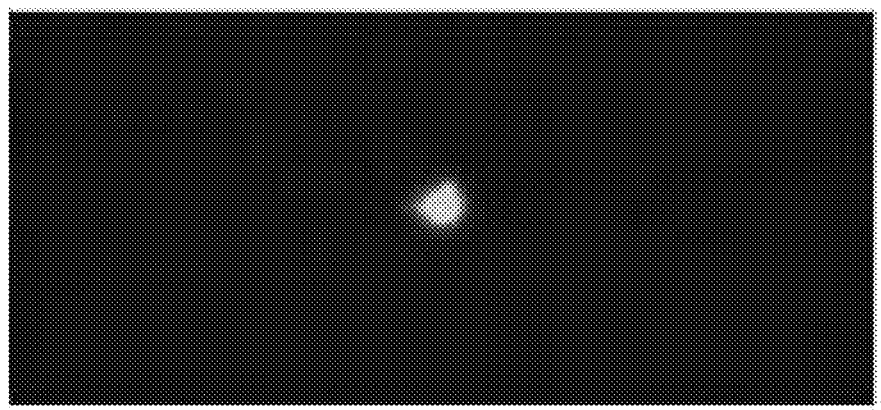
Figure 4D:
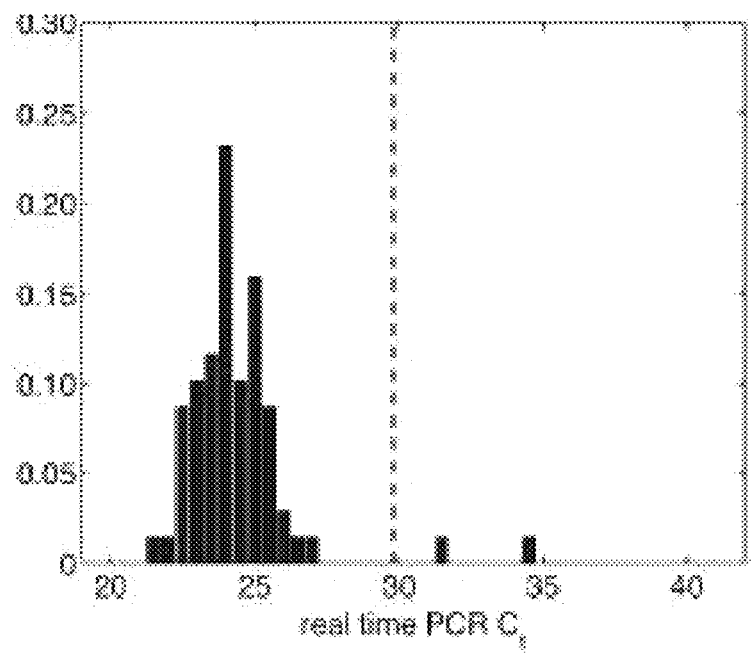
Figure 4E:
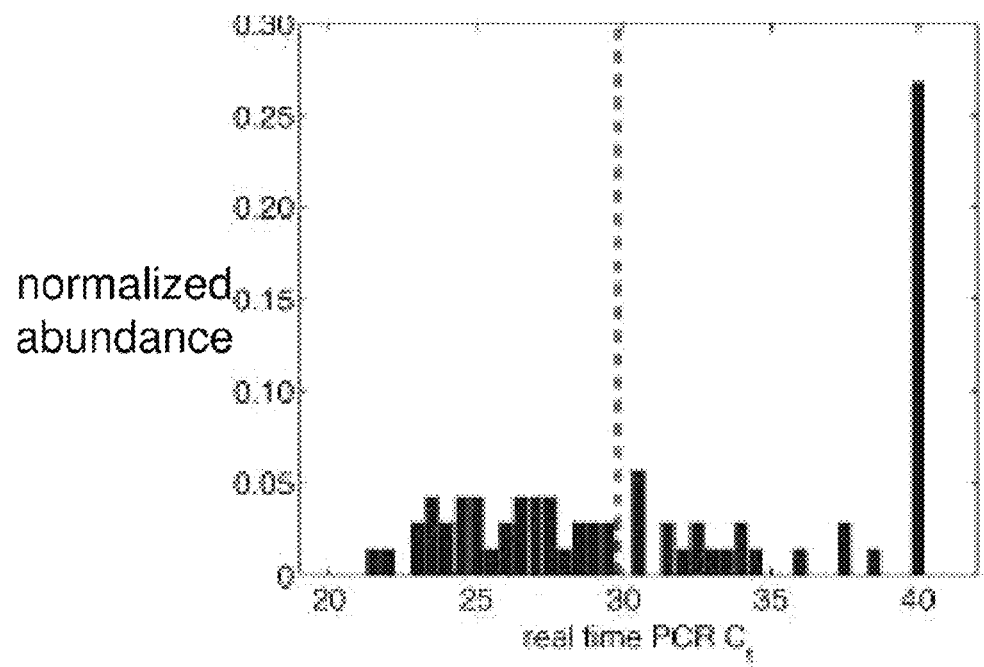

Although we provided seven guide RNAs at the same molar ratio, the plasmid transfection and replication process is likely quite stochastic. Some cells will inevitably receive different subsets or mixtures of the guide RNA cocktail, which might affect the treatment efficiency. To control for such effects, we measured EBV load at the single cell level by employing single-cell whole-genome amplification with an automated microfluidic system. We loaded freshly cultured Raji cells onto the microfluidic chip and captured 81 single cells (FIG. 4B). For the sgEBV1-7 treated cells, we flow sorted the live cells eight days after transfection and captured 91 single cells (FIG. 4C). Following manufacturer's instruction, we obtained ~150 ng amplified DNA from each single cell reaction chamber. For quality control purposes we performed 4-loci human somatic DNA quantitative PCR on each single cell amplification product (Wang J, Fan H C, Behr B, Quake S R (2012) Genome-wide single-cell analysis of recombination activity and de novo mutation rates in human sperm. Cell 150:402-412) and required positive amplification from at least one locus. 69 untreated single-cell products passed the quality control and displayed a log-normal distribution of EBV load (FIG. 4D) with almost every cell displaying significant amounts of EBV genomic DNA. We calibrated the quantitative PCR assay with a subclone of Namalwa Burkitt's lymphoma cells, which contain a single integrated EBV genome. The single-copy EBV measurements gave a Ct of 29.8, which enabled us to determine that the mean Ct of the 69 Raji single cell samples corresponded to 42 EBV copies per cells, in concordance with the bulk digital PCR measurement. For the sgEBV1-7 treated sample, 71 single-cell products passed the quality control and the EBV load distribution was dramatically wider (FIG. 4E). While 22 cells had the same EBV load as the untreated cells, 19 cells had no detectable EBV and the remaining 30 cells displayed dramatic EBV load decrease from the untreated sample.

Essential Targets For EBV Treatment. The seven guide RNAs in our CRISPR cocktail target three different categories of sequences which are important for EBV genome structure, host cell transformation, and infection latency, respectively. To understand the most essential targets for effective EBV treatment, we transfected Raji cells with subsets of guide RNAs. Although sgEBV4/5 reduced the EBV genome by 85%, they could not suppress cell proliferation as effectively as the full cocktail (FIG. 3A). Guide RNAs targeting the structural sequences (sgEBV1/2/6) could stop cell proliferation completely, despite not eliminating the full EBV load (26% decrease). Given the high efficiency of genome editing and the proliferation arrest (FIG. 2), we suspect that the residual EBV genome signature in sgEBV1/2/6 was not due to intact genomes but to free-floating DNA that has been digested out of the EBV genome, i.e. as a false positive. We conclude that systematic destruction of EBV genome structure appears to be more effective than targeting specific key proteins for EBV treatment.

Example 2

Targeting Hepatitis B Virus (HBV)

Methods and materials of the present invention may be used to apply targeted endonuclease to specific genetic material such as a latent viral genome like the hepatitis B virus (HBV). The invention further provides for the efficient and safe delivery of nucleic acid (such as a DNA plasmid) into target cells (e.g., hepatocytes). In one embodiment, methods of the invention use hydrodynamic gene delivery to target HBV.

Figure 10:
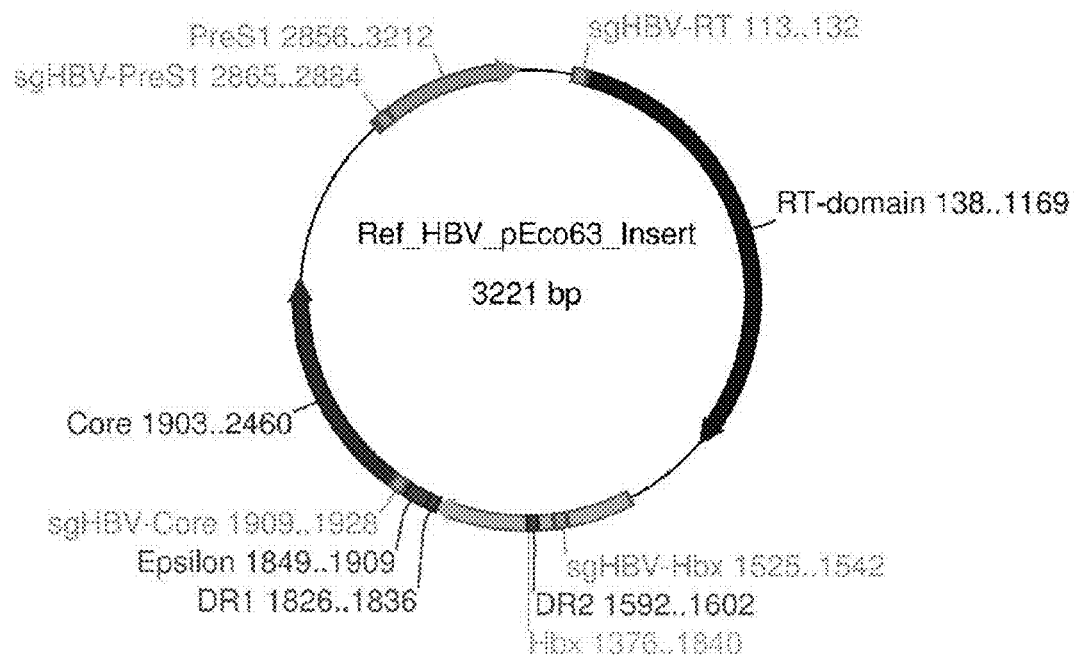
FIG. 10 is a map of an HBV genome.

FIG. 10 diagrams the HBV genome. It may be preferable to receive annotations for the HBV genome (i.e., that identify important features of the genome) and choose a candidate for targeting by enzymatic degredation that lies within one of those features, such as a viral replication origin, a terminal repeat, a replication factor binding site, a promoter, a coding sequence, and a repetitive region.

HBV, which is the prototype member of the family Hepadnaviridae, is a 42 nm partially double stranded DNA virus, composed of a 27 nm nucleocapsid core (HBcAg), surrounded by an outer lipoprotein coat (also called envelope) containing the surface antigen (HBsAg). The virus includes an enveloped virion containing 3 to 3.3 kb of relaxed circular, partially duplex DNA and virion-associated DNA-dependent polymerases that can repair the gap in the virion DNA template and has reverse transcriptase activities. HBV is a circular, partially double-stranded DNA virus of approximately 3200 bp with four overlapping ORFs encoding the polymerase (P), core (C), surface (S) and X proteins. In infection, viral nucleocapsids enter the cell and reach the nucleus, where the viral genome is delivered. In the nucleus, second-strand DNA synthesis is completed and the gaps in both strands are repaired to yield a covalently closed circular DNA molecule that serves as a template for transcription of four viral RNAs that are 3.5, 2.4, 2.1, and 0.7 kb long. These transcripts are polyadenylated and transported to the cytoplasm, where they are translated into the viral nucleocapsid and precore antigen (C, pre-C), polymerase (P), envelope L (large), M (medium), S (small)), and transcriptional trans-activating proteins (X). The envelope proteins insert themselves as integral membrane proteins into the lipid membrane of the endoplasmic reticulum (ER). The 3.5 kb species, spanning the entire genome and termed pregenomic RNA (pgRNA), is packaged together with HBV polymerase and a protein kinase into core particles where it serves as a template for reverse transcription of negative-strand DNA. The RNA to DNA conversion takes place inside the particles.

Numbering of basepairs on the HBV genome is based on the cleavage site for the restriction enzyme EcoR1 or at homologous sites, if the EcoR1 site is absent. However, other methods of numbering are also used, based on the start codon of the core protein or on the first base of the RNA pregenome. Every base pair in the HBV genome is involved in encoding at least one of the HBV protein. However, the genome also contains genetic elements which regulate levels of transcription, determine the site of polyadenylation, and even mark a specific transcript for encapsidation into the nucleocapsid. The four ORFs lead to the transcription and translation of seven different HBV proteins through use of varying in-frame start codons. For example, the small hepatitis B surface protein is generated when a ribosome begins translation at the ATG at position 155 of the adw genome. The middle hepatitis B surface protein is generated when a ribosome begins at an upstream ATG at position 3211, resulting in the addition of 55 amino acids onto the 5' end of the protein.

ORF P occupies the majority of the genome and encodes for the hepatitis B polymerase protein. ORF S encodes the three surface proteins. ORF C encodes both the hepatitis e and core protein. ORF X encodes the hepatitis B X protein. The HBV genome contains many important promoter and signal regions necessary for viral replication to occur. The four ORFs transcription are controlled by four promoter elements (preS1, preS2, core and X), and two enhancer elements (Enh I and Enh II). All HBV transcripts share a common adenylation signal located in the region spanning 1916-1921 in the genome. Resulting transcripts range from 3.5 nucleotides to 0.9 nucleotides in length. Due to the location of the core/pregenomic promoter, the polyadenylation site is differentially utilized. The polyadenylation site is a hexanucleotide sequence (TATAAA) as opposed to the canonical eukaryotic polyadenylation signal sequence (AATAAA). The TATAAA is known to work inefficiently (9), suitable for differential use by HBV.

There are four known genes encoded by the genome, called C, X, P, and S. The core protein is coded for by gene C (HBcAg), and its start codon is preceded by an upstream in-frame AUG start codon from which the pre-core protein is produced. HBeAg is produced by proteolytic processing of the pre-core protein. The DNA polymerase is encoded by gene P. Gene S is the gene that codes for the surface antigen (HBsAg). The HBsAg gene is one long open reading frame but contains three in-frame start (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. The function of the protein coded for by gene X is not fully understood but it is associated with the development of liver cancer. It stimulates genes that promote cell growth and inactivates growth regulating molecules.

With reference to FIG. 10, HBV starts its infection cycle by binding to the host cells with PreS1. Guide RNA against PreS1 locates at the 5' end of the coding sequence. Endonuclease digestion will introduce insertion/deletion, which leads to frame shift of PreS1 translation. HBV replicates its genome through the form of long RNA, with identical repeats DR1 and DR2 at both ends, and RNA encapsidation signal epsilon at the 5' end. The reverse transcriptase domain (RT) of the polymerase gene converts the RNA into DNA. Hbx protein is a key regulator of viral replication, as well as host cell functions. Digestion guided by RNA against RT will introduce insertion/deletion, which leads to frame shift of RT translation. Guide RNAs sgHbx and sgCore can not only lead to frame shift in the coding of Hbx and HBV core protein, but also deletion the whole region containing DR2-DR1-Epsilon. The four sgRNA in combination can also lead to systemic destruction of HBV genome into small pieces.

HBV replicates its genome by reverse transcription of an RNA intermediate. The RNA templates is first converted into single-stranded DNA species (minus-strand DNA), which is subsequently used as templates for plus-strand DNA synthesis. DNA synthesis in HBV use RNA primers for plus-strand DNA synthesis, which predominantly initiate at internal locations on the single-stranded DNA. The primer is generated via an RNase H cleavage that is a sequence independent measurement from the 5' end of the RNA template. This 18 nt RNA primer is annealed to the 3' end of the minus-strand DNA with the 3' end of the primer located within the 12 nt direct repeat, DR1. The majority of plus-strand DNA synthesis initiates from the 12 nt direct repeat, DR2, located near the other end of the minus-strand DNA as a result of primer translocation. The site of plus-strand priming has consequences. In situ priming results in a duplex linear (DL) DNA genome, whereas priming from DR2 can lead to the synthesis of a relaxed circular (RC) DNA genome following completion of a second template switch termed circularization. It remains unclear why hepadnaviruses have this added complexity for priming plus-strand DNA synthesis, but the mechanism of primer translocation is a potential therapeutic target. As viral replication is necessary for maintenance of the hepadnavirus (including the human pathogen, hepatitis B virus) chronic carrier state, understanding replication and uncovering therapeutic targets is critical for limiting disease in carriers.

In some embodiments, systems and methods of the invention target the HBV genome by finding a nucleotide string within a feature such as PreS1.

Guide RNA against PreS1 locates at the 5' end of the coding sequence. Thus it is a good candidate for targeting because it represents one of the 5'-most targets in the coding sequence. Endonuclease digestion will introduce insertion/deletion, which leads to frame shift of PreS1 translation. HBV replicates its genome through the form of long RNA, with identical repeats DR1 and DR2 at both ends, and RNA encapsidation signal epsilon at the 5' end.

The reverse transcriptase domain (RT) of the polymerase gene converts the RNA into DNA. Hbx protein is a key regulator of viral replication, as well as host cell functions. Digestion guided by RNA against RT will introduce insertion/deletion, which leads to frame shift of RT translation.

Guide RNAs sgHbx and sgCore can not only lead to frame shift in the coding of Hbx and HBV core protein, but also deletion the whole region containing DR2-DR1-Epsilon. The four sgRNA in combination can also lead to systemic destruction of HBV genome into small pieces. In some embodiments, method of the invention include creating one or several guide RNAs against key features within a genome such as the HBV genome shown in FIG. 10.

FIG. 10 shows key parts in the HBV genome targeted by CRISPR guide RNAs. To achieve the CRISPR activity in cells, expression plasmids coding cas9 and guide RNAs are delivered to cells of interest (e.g., cells carrying HBV DNA). To demonstrate in an in vitro assay, anti-HBV effect may be evaluated by monitoring cell proliferation, growth, and morphology as well as analyzing DNA integrity and HBV DNA load in the cells.

Figure 11:
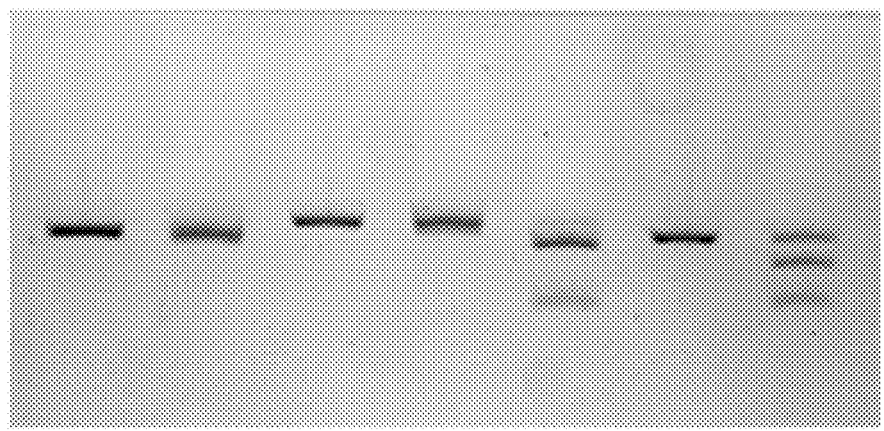
FIG. 11 shows the results of delivering a viral treatment.

The described method may be validated using an in vitro assay. To demonstrate, an in vitro assay is performed with cas9 protein and DNA amplicons flanking the target regions. Here, the target is amplified and the amplicons are incubated with cas9 and a gRNA having the selected nucleotide sequence for targeting. As shown in FIG. 11, DNA electrophoresis shows strong digestion at the target sites.

FIG. 11 shows a gel resulting from an in vitro CRISPR assay against HBV. Lanes 1, 3, and 6: PCR amplicons of HBV genome flanking RT, Hbx-Core, and PreS1. Lane 2, 4, 5, and 7: PCR amplicons treated with sgHBV-RT, sgHBV-Hbx, sgHBV-Core, sgHBV-PreS1. The presence of multiple fragments especially visible in lanes 5 and 7 show that sgHBV-Core and sgHBV-PreS1 provide especially attractive targets in the context of HBV and that use of systems and methods of the invention may be shown to be effective by an in vitro validation assay.

What is claimed is:

1. A method for treating an infection by a virus, the method comprising:
   introducing into a cell a vector comprising an origin of replication of the virus, said origin of replication is not transcribed to generate a sequence-specific targeting moiety, a sequence encoding a nuclease, and a sequence encoding a sequence-specific targeting moiety that targets the nuclease to a genome of the virus;
   targeting the nuclease to a viral nucleic acid within the genome of the virus by means of the sequence-specific targeting moiety; and
   cleaving the viral nucleic acid with the nuclease without interfering with the host genome.

2. The method of claim 1, wherein the nuclease is selected from the group consisting of a zinc-finger nuclease, a transcription activator-like effector nuclease, and a meganuclease.

3. The method of claim 1, wherein the nuclease is a Cas9 nuclease and the sequence-specific targeting moiety comprises a guide RNA.

4. The method of claim 1, wherein the viral nucleic acid is latent in a host cell.

5. The method of claim 1, wherein said cleaving step comprises creating a double-strand break in said viral nucleic acid.

6. The method of claim 1, further comprising the step of inserting a polynucleotide into the viral nucleic acid.

7. The method of claim 1, wherein the viral nucleic acid is from a virus selected from the group consisting of adenovirus, herpes simplex virus, varicella-zoster virus, Epstein-Barr virus, human cytomegalovirus, human herpesvirus type 8, human papillomavirus, BK virus JC virus, and smallpox.

8. The method of claim 1, wherein the vector is a viral vector selected from the group consisting of retrovirus, lentivirus, adenovirus, herpesvirus, poxvirus, alphavirus, vaccinia virus, and adeno-associated viruses.

9. The method of claim 1, wherein the vector is introduced into the cell via a non-viral vector.

10. The method of claim 9, wherein said non-viral vector is selected from the group consisting of a nanoparticle, a cationic lipid, a cationic polymer, a metallic nanoparticle, a nanorod, a liposome, microbubbles, a cell-penetrating peptide, and a liposphere.

11. The method of claim 9, wherein the non-viral vector comprises polyethyleneglycol.

12. The method of claim 1, wherein the vector is a plasmid.

13. The method of claim 12, wherein the nuclease is a Cas9 nuclease and the sequence-specific targeting moiety comprises a guide RNA.

14. The method of claim 13, wherein the viral nucleic acid is latent in a host cell.

15. The method of claim 14, wherein the viral nucleic acid is from Epstein-Barr virus.

16. The method of claim 15, wherein the cleaving step comprises creating a double-strand break in the viral nucleic acid.

17. A method for treating an infection by a virus, the method-comprising:
   introducing into a cell a plasmid that comprises an origin of replication of the virus, said origin of replication is not transcribed to generate a guide RNA, a sequence encoding a Cas9 nuclease, and a sequence encoding a guide RNA that targets a portion of a genome of the virus;
   targeting the Cas9 nuclease to the portion of the genome of the virus by means of the guide RNA; and
   cleaving the genome of the virus with the Cas9 nuclease without interfering with the host genome.

18. The method of claim 17, further comprising increasing copy number of the plasmid preferentially in cells infected by the virus by means of the viral origin of replication of the virus.

19. The method of claim 18, wherein the portion of the genome of the virus comprises a 20 nucleotide segment 5' to a protospacer adjacent motif within the genome of the virus, and wherein a portion of the guide RNA is at least 60% complementary to the portion of the genome of the virus, and wherein the portion of the guide RNA has no match in a human genome.

20. The method of claim 18, wherein the guide RNA binds to the genome of the virus within a latency-related target.

* * * * *